US006126870A

United States Patent [19]
Akhavan-Tafti

[11] Patent Number: 6,126,870
[45] Date of Patent: *Oct. 3, 2000

[54] CHEMILUMINESCENT LABELING COMPOUNDS

[75] Inventor: Hashem Akhavan-Tafti, Howell, Mich.

[73] Assignee: Lumigen, Inc., Southfield, Mich.

[*] Notice: This patent is subject to a terminal disclaimer.

[21] Appl. No.: 09/099,657

[22] Filed: Jun. 17, 1998

Related U.S. Application Data

[63] Continuation-in-part of application No. 08/927,381, Sep. 12, 1997.
[51] Int. Cl.$^7$ .......................... C09K 3/00; C07D 219/04; G01N 33/53
[52] U.S. Cl. .......................... 252/700; 546/102; 546/103; 546/104; 544/96; 544/212; 435/4; 435/5; 435/6; 435/7.1
[58] Field of Search .................. 252/700; 435/4, 435/5, 6, 7.1; 546/102, 103, 104; 544/96, 212

[56] References Cited

U.S. PATENT DOCUMENTS 5,772,926  6/1998  Akhavan-Tafti ................... 252/700

*Primary Examiner*—Philip Tucker
*Attorney, Agent, or Firm*—Richard S. Handley

[57] ABSTRACT

Chemiluminescent labeling compounds and chemiluminescent labeled conjugates are provided. The compounds comprise an acridan ring bearing an exocyclic double bond and further contain a labeling substituent which permits attachement to compounds of interest. The novel chemiluminescent compounds and labeled conjugates generated chemiluminescence rapidly after undergoing a reaction with an acid, an oxidant and a base. The compounds and conjugates are useful in assays of an analyte in a sample and in assays employing labeled specific binding pairs.

22 Claims, 3 Drawing Sheets

650 130 26 5.2 1.0 ng OF PROTEIN 880 176 35 7.0 1.4 ng OF PROTEIN

CHEMILUMINESCENT LABELING COMPOUNDS

CROSS REFERENCE TO RELATED APPLICATION

This application is a continuation-in-part of applicants' co-pending U.S. application Ser. No. 08/927,381 filed on Sep. 12, 1997.

FIELD OF THE INVENTION

The present invention relates to a new method of rapidly producing chemiluminescence from electron-rich alkenes by a simple chemical process using inexpensive, readily available reagents. The present invention relates further to chemiluminescent labeling compounds, their use in preparing chemiluminescent labeled compounds and the use of the labeled compounds in assay methods. The invention further relates to assay methods for detecting an analyte and for detecting chemiluminescent-labeled analyte, especially within an electrophoresis gel. The methods are useful in immunoassays, nucleic acid probe assays and the like.

BACKGROUND OF THE INVENTION

Chemiluminescent detection of analytes has assumed increasing importance in a number of fields, including biomedical analysis, food testing, pathogen identification, forensic investigations and enviromental contaminant screening. The means of incorporating a chemiluminescent endpoint into a test or assay can take different forms, such as a chemiluminescent substrate for an enzyme label, a chemiluminescent compound shielded within a structure such as a micelle, liposome or latex particle or by using a chemiluminescent compound as a label. Numerous compounds have been devised for these purposes (R. Handley, H. Akhavan-Tafti, A. P. Schaap, J. Clin. Ligand Assay, 20(4) 302–312 (1997)). The use of chemiluminescent compounds to label species to be detected with small molecules has attracted interest due to the ability to attach multiple labels and to generate the chemiluminescence rapidly. Nevertheless, no single labeling and detection scheme has has proven superior in all applications.

Chemiluminescent Labels Luminol, isoluminol and related cyclic diacyl hydrazides were the first chemiluminescent compounds to be adapted as direct labels by modifying their structure to include a linking substituent. Their use is not satisfactory for many applications due to insufficient light generation limiting detection sensitivity. The low chemiluminescence quantum efficiency, 0.1–1%, and times as long as several minutes for all of the photons to be emitted diminish instantaneous light intensity.

Acridinium esters and acridinium sulfonamides have been used extensively in chemiluminescent immunoassays. (See, e.g., U.S. Pat. Nos. 5,656,500, 5,521,103 and references cited therein). The principal advantages of these labels are the high yield of chemiluminescence (ca. 10%) coupled with the short duration of emission, typically 1–2 sec. Liberating the light energy in such a short flash creates high light intensities. The use of these labels, however, suffers from certain serious drawbacks. Acridinium esters and to a lesser extent the sulfonamides, are prone to hydrolysis to the nonluminescent carboxylic acid, the hydrolysis being accelerated at alkaline pH. The well-known problem of pseudo-base formation from attack of water at the 9-position on the ring requires a separate reaction step to regenerate the acridinium ring.

Ruthenium or osmium-containing complexes produce chemiluminescence when oxidized electrochemically in the presence of a sacrificial amine electron donor. The reaction requires a more costly and complex instrument for performing the electrochemical and light detection steps simultaneously.

While many large molecules are used as labels, including enzymes and the photoprotein aequorin, their use suffers the disadvantage of limiting the number of labels which can be attached to the target species and having the tendency of depositing non specifically on supports and surfaces.

It remains a goal of the assay field to develop chemiluminescent labeling compounds which are small, water-soluble molecules, have high chemiluminescence efficiencies, emit the light rapidly upon reaction with simple chemical activating agents, are stable on extended storage and not subject to side reactions. The present invention provides such compounds.

Labeling Procedures. A wide variety of procedures for chemically binding labels to organic and biological molecules are described in the literature (see, for example: L. J. Kricka, *Ligand-Binder Assays,* Marcel Dekker, Inc., New York, 1985, pp. 15–51 and M. Z. Atassi, "Chemical Modification and Cleavage of Proteins," Chapter 1 in *Immunochemistry of Proteins,* Vol. 1, Plenum Press, New York, 1977, pp. 1–161, and references therein). Antibodies and proteins are conveniently labeled by reaction of certain nucleophilic groups present in proteins (—SH, —OH, —$NH_2$, —COOH) with chemically reactive groups. Appropriately functionalized nucleic acids and DNA probes can also be labeled by reaction with the corresponding reactive group on a label. Many other types of molecules which can be labeled including antibodies, enzymes, protein antigens, peptides, haptens, steroids, carbohydrates, fatty acids, hormones, nucleosides and nucleotides.

Chemiluminescent Detection in Gels. A method for the detection of the enzyme alkaline phosphatase in a gel using a chemiluminescent substrate has been described (N. Theodosiou, C. Chalot, C. Ziomek, BioTechniques, 13(6), 898–901(1992)). Applicant is unaware of any report of the electrophoretic separation and chemiluinescent detection of a chemiluminescent labeled compound in a gel.

SUMMARY OF THE INVENTION

It is an object of the present invention to provide methods for generating chemiluminescence from a chemiluminescent compound by a simple chemical process using inexpensive, readily available reagents.

It is yet another object of the present invention to provide assay methods by means of a simple chemiluminescent reaction.

It is a further object of the present invention to provide labeling compounds for preparing chemiluminescent labeled compounds.

It is another object of the present invention to provide chemiluminescent labeled compounds.

It is also an object of the present invention to provide labeling compounds of formula I wherein Z1 and Z2 are independently selected from nitrogen, oxygen and sulfur.

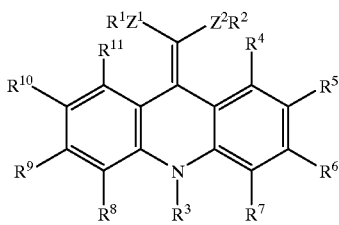

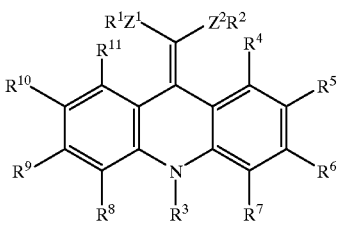

It is a further object of the present invention to provide methods for generating chemiluminescence from the chemiluminescent label itself or the chemiluminescent labeled compound.

It is a still a further object of the present invention to provide a method for detecting an analyte in a gel by providing a chemiluminescent labeled compound for detection, subjecting it to an electrophoretic separation in a gel and detecting it by a chemiluminescent reaction directly in the gel.

It is yet another object of the present invention to provide chemiluminescent methods for conducting an assay using chemiluminescent labeled compounds. Representative assays include immunoassays, nucleic acid hybridization assays, other ligand-binder assays, detection of analytes in food, environmental and industrial samples.

GENERAL DESCRIPTION

Modern biomedical analyses require the ability to detect very small amounts of compounds due either to low abundance of the analyte in the sample or to limited sample quantity. In addition it must be possible to detect the quantity of the compound precisely over a very wide range of concentrations. Chemiluminescent labeling compounds and methods are disclosed herein which are suitable for these types of analyses.

The present invention relates generally to methods of generating chemiluminescence and compounds for use in these methods. The methods use acridan compounds and simple, inexpensive and readily available reagents for generating chemiluminescence therefrom. The light producing reaction can be used for a number of art-recognized purposes, including analytical methods of assay, signaling, emergency lighting and novelty items.

The present invention also involves chemiluminescent labeling compounds which can be bound to organic and biological molecules by chemical bonds or through physical interactions for the purpose of performing an assay. Reaction of the chemiluminescent compounds of the present invention according to the presently described methods produces chemiluminescence as visible light. The intensity of the resulting chemiluminescence provides a direct measure of the quantity of the chemiluminescent label and, therefore, of the labeled compound.

The present invention further involves a method for detecting a chemiluminescent labeled compound in an electrophoresis gel of the type used in separating biological molecules. Chemiluminescent labeled compounds of the present invention can be applied to a gel, separated electrophoretically and subsequently be detected in the gel without the need for transfer to a blotting membrane.

The acridan compounds useful in the methods of the invention have formula I wherein at least one of the groups $R^1$–$R^{11}$ can be a labeling substituent of the formula

L is a linking group which can be a bond or another divalent or polyvalent group, RG is a reactive group which enables the chemiluminescent labeling compound to be bound to another compound, $Z^1$ and $Z^2$ are independently selected from O, S and $NR^{12}$, $R^{12}$ is selected from alkyl, aryl, alkylsulfonyl and arylsulfonyl groups, $R^1$ is a group removable by an acid, $R^2$ and $R^3$ are organic groups containing from 1 to 50 non-hydrogen atoms, and each of $R^4$–$R^{11}$ is hydrogen or a noninterfering substituent.

BRIEF DESCRIPTION OF THE DRAWINGS

FIG. 3A shows the detection of BSA—$APNa_2$.

DESCRIPTION OF THE PREFERRED EMBODIMENTS

Figure 1:
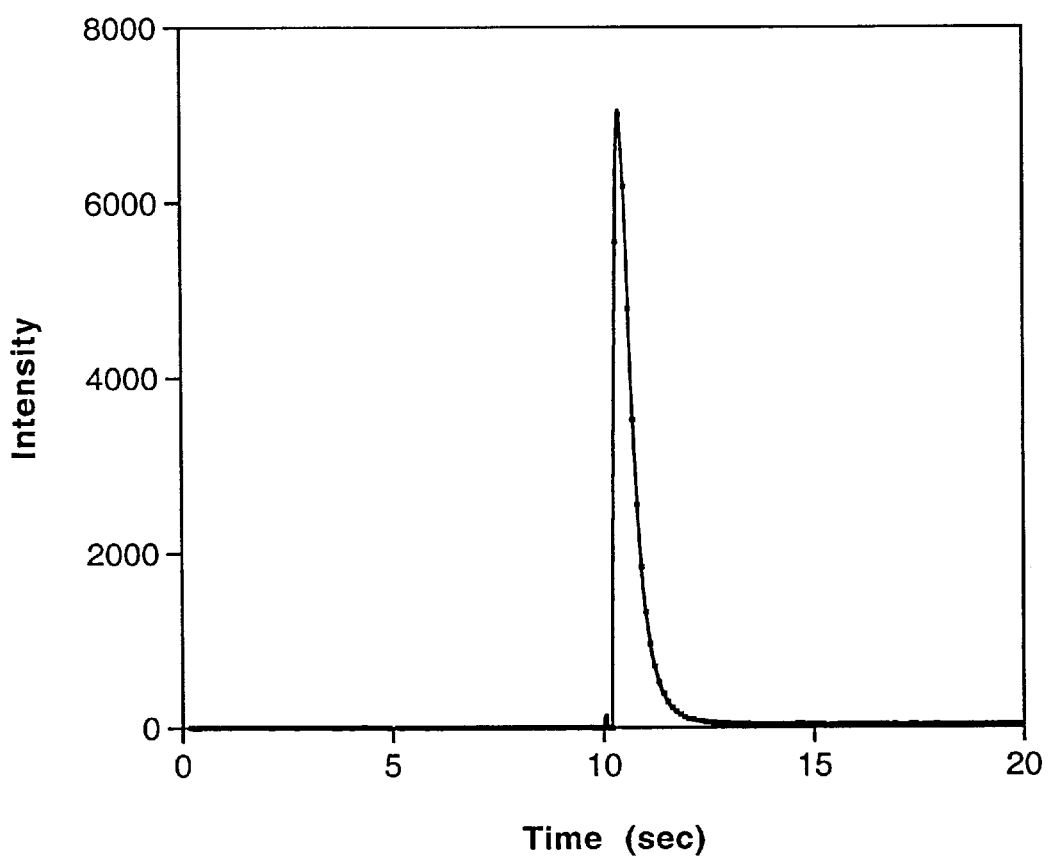
FIG. 1 is a graph showing the time profile of chemiluminescence resulting from reaction of acridan phosphate 5. Light production ensued upon mixing and reached maximum intensity in under 1 s.

Definitions:

Acid—A compound which, when added to water, causes a decrease in the pH of the resulting solution. Acid as used herein includes mineral acids, such as hydrochloric, nitric, sulfuric and perchloric, organic acids, including carboxylic acids such as oxalic, acetic and propionic, and other types of organic compounds, such as picric acid and Lewis acids, such as aluminum chloride, ferric chloride and the like.

Alkyl—A branched, straight chain or cyclic hydrocarbon group containing from 1–20 carbons. Lower alkyl as used herein refers to those alkyl groups containing up to 8 carbons.

Alkenyl—A branched, straight chain or cyclic hydrocarbon group containing at least one C—C double bond and containing from 2–20 carbons. Lower alkenyl as used herein refers to those alkenyl groups containing up to 8 carbons.

Alkynyl—A branched or straight chain hydrocarbon group containing at least one C—C triple bond and containing from 2–20 carbons. Lower alkynyl as used herein refers to those alkynyl groups containing up to 8 carbons.

Analyte—A substance the presence or amount of which is to be measured in a sample by an assay. Analytes include organic and biological molecules to which a specific binding partner having a specific binding affinity exists. Exemplary analytes include, without limitation, single stranded or double stranded DNA, RNA, DNA-RNA complexes, oligonucleotides, antibodies, antibody fragments, antibody-DNA chimeras, antigens, haptens, proteins, lectins, avidin, streptavidin and biotin. Other exemplary analytes also include drugs, hormones and pesticides.

Aryl—An aromatic ring-containing group containing 1 to 5 carbocyclic aromatic rings, which can be substituted with 1 or more substituents other than H.

Biomedical analysis—Analyses of samples of biological origin for analytes of interest. The analyses can be immunoassays, western blots, northern blots, Southern blots, DNA hybridization assays, DNA sequence analysis, colony hybridizations, gene expression analysis, high throughput drug screening, detection of infectious agents or pathogens and the like.

Glycosyl—Residues of carbohydrate groups including hexoses and pentoses and contain one or more sugar unit. Examples include fructose, galactose, glucose, glucuronate, mannose, ribose, N-acetylglucosamine and the like.

Halogen—Fluorine, chlorine, bromine or iodine atoms.

Heteroaryl—An aromatic ring-containing group containing 1 to 5 carbocyclic aromatic rings in which at least one of the ring carbon atoms is replaced with a nitrogen, oxygen or sulfur atom and which can be substituted with 1 or more substituents other than H.

Luminescent—capable of emitting light when excited to an electronic excited state. The light can be emitted either as fluorescence when decaying from a singlet excited state or as phosphorescence when decaying from a triplet excited state.

Peroxide—A compound containing an O—O bond, preferably hydrogen peroxide or a complex of hydrogen peroxide such as urea peroxide, perborate or percarbonate.

Alkyl

Sample—A fluid containing or suspected of containing one or more analytes to be assayed. Typical samples which are analyzed by the chemiluminescent reaction method are biological samples including body fluids such as blood, plasma, serum, urine, semen, saliva, cell lysates, tissue extracts and the like. Other types of samples include food samples and environmental samples such as soil or water.

Specific binding pair—Two substances which exhibit a mutual binding affinity. Examples include antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

Substituted—Refers to the replacement of at least one hydrogen atom on a group by another atom or a group having from 1 to 50 atoms selected from C, O, N, S, P, Si, B, Se, F, Cl, Br and I. It should be noted that in references to substituted groups it is intended that multiple points of substitution can be present unless indicated otherwise.

It has been unexpectedly discovered that chemiluminescent compounds of formula I below undergo a reaction with certain reagents to generate chemiluminescence as a brief, intense flash of light. Use of the present compounds for detection, e.g. as labels, in chemiluminescent assays leads to highly sensitive detection of analytes. Chemiluminescent compounds of the present invention have formula I:

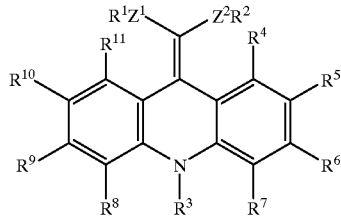

I wherein $Z^1$ and $Z^2$ are independently selected from O, S and $NR^{12}$, $R^{12}$ is selected from alkyl, aryl, alkylsulfonyl and arylsulfonyl groups, $R^1$ is a group containing from 1 to about 50 non-hydrogen atoms which is removable by an acid and $R^2$ and $R^3$ are organic groups containing from 1 to 50 non-hydrogen atoms selected from C, N, O, S, P and halogen atoms, $R^4$–$R^{11}$ are independently selected from hydrogen and substituents which do not interfere with the generation of chemiluminescence, and at least one of the groups $R^1$–$R^{11}$ can be a labeling substituent. When a labeling substituent is present it is preferably one of $R^1$ or $R^2$.

Methods of Generating Chemiluminescence. In the present methods for producing chemiluminescence, a compound of formula I undergoes a reaction comprising the steps of:

a) contacting the compound of formula I with an acid to form a first reaction product; and b) contacting the first reaction product with a sufficient quantity of a base to provide a basic environment, at least one of the steps including providing an oxidant for reaction, wherein a second reaction product is formed and the light is produced in the basic environment. Light intensity reaches a maximum level rapidly, often within a second or less, at room temperature when the reaction is conducted at alkaline pH.

The acid used in the first step must be capable of providing a low pH environment, at least below about 3 and preferably not greater than 1. Mineral acids are preferred because of their low cost and high acidity. In some instances, oxidizing mineral acids, e.g., nitric acid may be preferred. Acids will typically be used at a concentration in the range 0.001M to 1M.

The oxidant can be a peroxide or alkyl hydroperoxide. Preferred peroxides include hydrogen peroxide, urea peroxide, persulfate and perborate salts. The oxidant can also be a metal oxide such as $CrO_3$, $MnO_2$ or an anionic complex such as periodate $IO_4^-$ or permanganate $MnO_4^-$, or a metal peroxide such as $Na_2O_2$. Other oxidants include heme or hemoglobin. The acid can also function, in part, as an oxidant, as for example, when the acid is nitric acid. The choice of whether it is preferred to combine the oxidant with the acid in the first step or the base in the second step is influenced by the choice of the acid and the stability and reactivity of the oxidant in the base. In general, it may be advantageous to combine the oxidant with the base when the acid is an oxidizing acid. In other cases, it may be advantageous to combine the oxidant with the acid.

Basic compounds useful in the practice of the present invention comprise compounds which, when added to water causes an increase in the pH of the resulting solution. This includes include hydroxide salts, such as sodium, potassium or lithium hydroxide, ammonium hydroxide and tetraalkylammonium hydroxide, carbonates and basic metal oxides. The use of organic bases is also contemplated. The preferred bases are the alkali metal hydroxides.

The reaction is typically performed at a temperature between 5° C. and 50° C., preferably between 20° C. and 40°

C., and usually at ambient temperature. The reaction of the present invention is carried out in aqueous solution which may be in contact with the surface of a solid support such as a bead, tube, membrane or microwell plate coated with peroxidase. In some assay formats, it may be desirable to perform assay steps involving binding reactions in buffer solution. The acid must be used in a quantity and concentration sufficient to overcome the buffering capacity and lower the solution pH to not more than 3 and preferably about 1 or lower.

Chemiluminescent Assay Methods. Another aspect of the present invention is the use of the chemiluminescent reaction in a method to detect an analyte, comprising generating the light by the chemiluminescent reaction, detecting the light produced and, if quantitation is desired, relating the amount of light produced to the amount of the analyte. The relationship between light intensity and amount of analyte can be easily discerned by constructing a calibration curve with known amounts of the chemiluminescent compound. The overall chemiluminescent reaction can be illustrated by the reaction below.

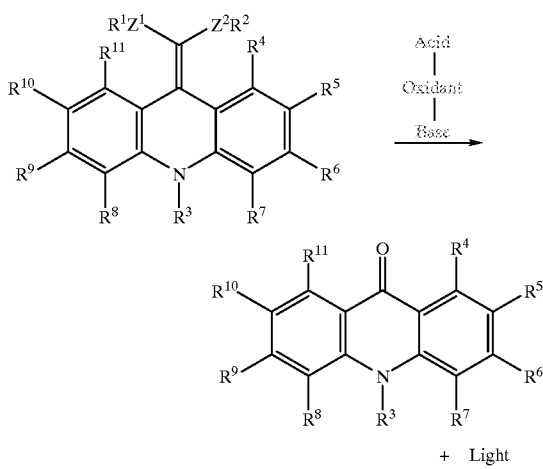

In some assay formats, the compound of formula I may not bear a labeling substituent, but rather be associated with the analyte by other means. For example, the chemiluminescent compound may be encapsulated within a liposome or latex particle which, in turn, bears a labeling substituent or specific binding partner. Examples of the latter include liposome-antibody conjugtes, liposome oligonucleotide conjugates, particle-antibody, particle antigen and particle DNA conjugates. Contacting the liposome or latex particle with the acid, oxidant and base with the chemiluminescent liposome or particle allows the chemiluminescent reaction to occur for detecting the analyte. In other preferred assay formats, the compound of formula I will bear a labeling substituent to allow attachment to an analyte, or a specific binding pair member.

In other preferred assay formats, the compound of formula I is used as a chemiluminescent labeling compound for the purpose of providing a chemiluminescent label on a compound to be detected. In these assays, the compound of formula I will further comprise a labeling substituent of the formula —L—RG, wherein L is a linking group which is optional and, when present, is provided to connect the chemiluminescent moiety to a reactive group, RG.

Chemiluminescent Compounds. In the compounds of formula I, the group $R^1$ is a group which, when attached to a $Z^1$-substituted double bond, can be removed by an acid, and can be any group containing from 1 to about 50 non-hydrogen atoms selected from C, N, O, S, P, Si and halogen atoms. Preferred groups are selected from substituted or unsubstituted alkyl, substituted or unsubstituted aryl, substituted or unsubstituted aralkyl groups of 1–20 carbon atoms, substituted or unsubstituted alkyl or aryl carbonyl groups having from 1–20 carbon atoms, tri($C_1$–$C_8$ alkyl)silyl groups, an $SO_3^-$ group, glycosyl groups and phosphoryl groups of the formula PO(OR') (OR") wherein R' and R" are independently selected from hydrogen, substituted or unsubstituted alkyl, substituted or unsubstituted aryl, substituted or unsubstituted aralkyl groups of 1–20 carbon atoms, trialkylsilyl groups, alkali metal cations, alkaline earth cations, ammonium and phosphonium cations. A preferred $R^1$ group is a phosphate salt group $PO_3M_2$ with M being an alkali metal ion.

The group $R^2$ can be any group containing from 1 to about 50 non-hydrogen atoms selected from C, N, O, S, P, Si and halogen atoms which allows light production. By the latter is meant that when a compound of formula I is undergoes a reaction of the present invention, the light is produced and can involve the production of one or more chemiluminescent intermediates. $R^2$ is preferably selected from substituted or unsubstituted alkyl, substituted or unsubstituted aryl, substituted or unsubstituted aralkyl groups of 1–20 carbon atoms, substituted or unsubstituted alkyl or aryl carbonyl groups having from 1–20 carbon atoms, tri($C_1$–$C_8$ alkyl) silyl groups, an $SO_3^-$ group, glycosyl groups and phosphoryl groups of the formula PO(OR') (OR") wherein R' and R" are independently selected from hydrogen, substituted or unsubstituted alkyl, substituted or unsubstituted aryl and substituted or unsubstituted aralkyl groups of 1–20 carbon atoms, trialkylsilyl groups, alkali metal cations, alkaline earth cations, ammonium and phosphonium cations. Exemplary substituted alkyl groups include a cyanoethyl group or a trimethylsilylethyl group. In a preferred embodiment, $R^2$ is an aryl group, preferably phenyl, substituted with the labeling substituent of the formula —L—RG.

The group $R^3$ is an organic group containing from 1 to 50 atoms non-hydrogen atoms selected from C, N, O, S, P, Si and halogen atoms in addition to the necessary number of H atoms required satisfy the valencies of the atoms in the group. More preferably $R^3$ contains from 1 to 20 non-hydrogen atoms. The organic group is preferably selected from the group consisting of alkyl, substituted alkyl, aryl, substituted aryl and aralkyl groups. More preferred groups for $R^3$ include substituted or unsubstituted $C_1$–$C_4$ alkyl groups, substituted or unsubstituted benzyl groups, alkoxyalkyl, carboxyalkyl and alkylsulfonic acid groups. The group $R^3$ can be joined to either $R^7$ or $R^8$ to complete a 5 or 6-membered ring.

In the compounds of formula I, the groups $R^4$–$R^{11}$ each are independently H or a substituent group which permits the light to be produced and generally contain from 1 to 50 atoms selected from C, N, O, S, P, Si and halogen atoms. Representative substituent groups which can be present include, without limitation, alkyl, substituted alkyl, aryl, substituted aryl, aralkyl, alkenyl, alkynyl, alkoxy, aryloxy, halogen, amino, substituted amino, carboxyl, carboalkoxy, carboxamide, cyano, and sulfonate groups. Pairs of adjacent groups, e.g. $R^4$–$R^5$ or $R^5$–$R^6$, can be joined together to form a carbocyclic or heterocyclic ring system comprising at least one 5 or 6-membered ring which is fused to the ring to which the two groups are attached. Such fused heterocyclic rings can contain N, O or S atoms and can contain ring substituents other than H such as those mentioned above. One or more of the groups $R^4$–$R^{11}$ can be a labeling substituent of the formula —L—RG. It is preferred that $R^4$ to $R^{11}$ are selected from hydrogen, halogen and alkoxy groups such as methoxy, ethoxy, t-butoxy and the like. A preferred group of compounds has one of $R^5$, $R^6$, $R^9$ or $R^{10}$ as a halogen and the other of $R^4$ to $R^{11}$ are hydrogen atoms.

Substituent groups can be incorporated in various quantities and at selected ring or chain positions in the acridan ring in order to modify the properties of the compound or to provide for convenience of synthesis. Such properties include, e.g. chemiluminescence quantum yield, rate of reaction with the enzyme, maximum light intensity, duration of light emission, wavelength of light emission and solubility in the reaction medium. Specific substituents and their effects are illustrated in the specific examples below, which, however, are not to be considered limiting the scope of the invention in any way.

Linking group (L). The linking group can be a bond, an atom, or a straight, or branched chain of atoms some of which can be part of a ring structure. The substituent usually contains from 1 to about 50 non-hydrogen atoms, more usually from 1 to about 30 non-hydrogen atoms. Atoms comprising the chain are selected from C, O, N, S, P, Si, B, and Se atoms, preferably from C, O, N, P and S atoms. Halogen atoms can be present as substituents on the chain or ring. Typical functional groups comprising the linking substituent include alkylene, arylene, alkenylene, ether, peroxide, carbonyl as a ketone, ester, carbonate ester, thioester, or amide group, amine, amidine, carbamate, urea, imine, imide, imidate, carbodiimide, hydrazine, diazo, phosphodiester, phosphotriester, phosphonate ester, thioether, disulfide, sulfoxide, sulfone, sulfonate ester, sulfate ester, and thiourea groups.

Reactive group. The reactive group RG is an atom or group whose presence facilitates bonding to another molecule by covalent attachment or physical forces. In some embodiments, attachment of a chemiluminescent labeling compound of the present invention to another compound will involve loss of one or more atoms from the reactive group for example when the reactive group is a leaving group such as a halogen atom or a tosylate group and the chemiluminescent labeling compound is covalently attached to another compound by a nucleophilic displacement reaction. In other embodiments, attachment of a chemiluminescent labeling compound to another compound by covalent bond formation will involve reorganization of bonds within the reactive group as occurs in an addition reaction such as a Michael addition or when the reactive group is an isocyanate or isothiocyanate group. In still other embodiments, attachment will not involve covalent bond formation, but rather physical forces in which case the reactive group remains unaltered. By physical forces is meant attractive forces such as hydrogen bonding, electrostatic or ionic attraction, hydrophobic attraction such as base stacking, and specific affinity interactions such as biotin-streptavidin, antigen-antibody and nucleotide-nucleotide interactions.

TABLE 1

Reactive Groups for Chemical Binding of Labels to Organic and Biological Molecules a.) Amine reactive groups

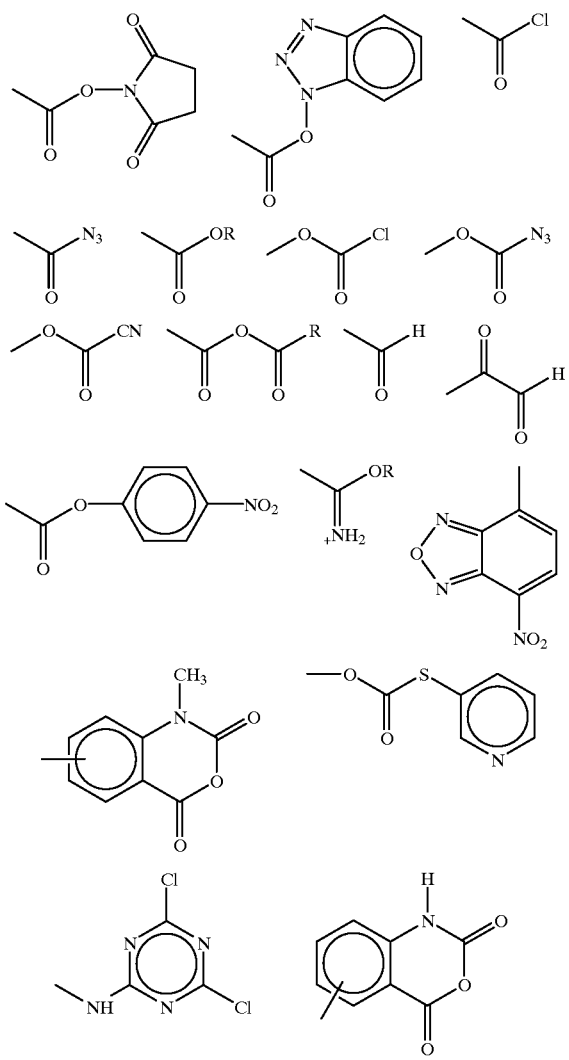

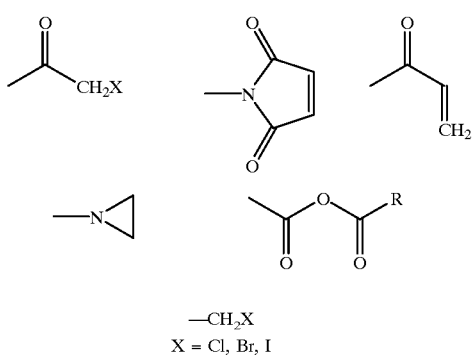

b.) Thiol reactive groups

—$CH_2X$
X = Cl, Br, I

TABLE 1-continued

Reactive Groups for Chemical Binding of Labels to Organic and Biological Molecules

[chemical structures shown]

3) Carboxylic acid reactive groups

—NH₂  —OH  —NHNH₂

4) Hydroxyl reactive groups

[chemical structures shown]

—N=C=S  —SO₂Cl
—N=C=O  —SO₂CH₂CF₃

[chemical structures shown]

X = Cl, Br, I

[chemical structures shown]

—N=C=S  —SO₂Cl
—N=C=O  —SO₂CH₂CF₃

Preferred reactive groups include OH, NH₂, COOH, SO₂CH₂CF₃ N-hydroxysuccinimide ester and maleimide groups.

Bifunctional coupling reagents can also be used to couple labels to organic and biological molecules with moderately reactive groups (see L. J. Kricka, *Ligand-Binder Assays,* Marcel Dekker, Inc., New York, 1985, pp. 18–20, Table 2.2 and T. H Ji, "Bifunctional Reagents," *Methods in Enzymology,* 91, 580–609 (1983)). There are two types of bifunctional reagents, those which become incorporated into the final structure and those which do not and serve only to couple the two reactants.

A preferred group of compounds have formula II wherein each of $R^4$ to $R^{11}$ are hydrogen. The groups $Z^1$, $Z^2$, $R^1$, $R^2$ and $R^3$ are as defined above.

II

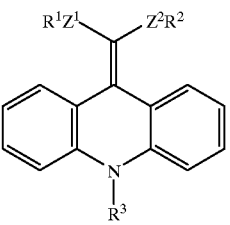

Another preferred class of compounds has the formula III below wherein $Z^1$ together with $R^1$ is a phosphate group, $Z^2$ is selected from O, S and $NR^{12}$, $R^2$, $R^3$ and $R^4$–$R^{11}$ are as defined above and R'and R"are independently selected from alkyl groups, substituted alkyl groups and alkali metal ions.

III

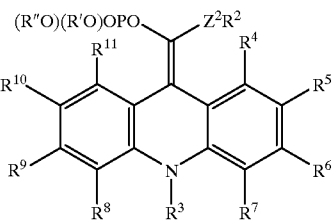

Preferred compounds of formula III have hydrogen atoms for each of $R^4$–$R^{11}$ is hydrogen and $R^3$ is an alkyl group, more preferably a lower alkyl. More preferred is a compound of formula IV.

IV

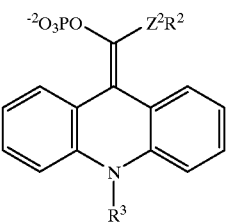

Preferred labeling compounds have formulas V–X

V

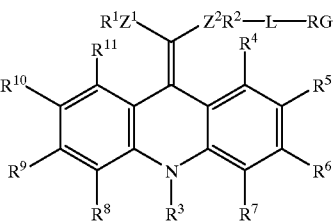

VI 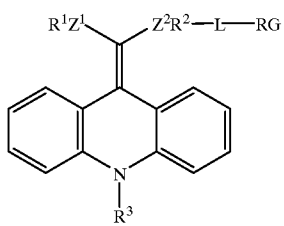

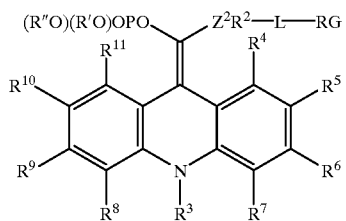
VII

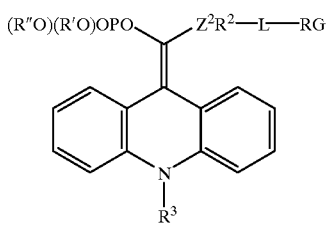
VIII

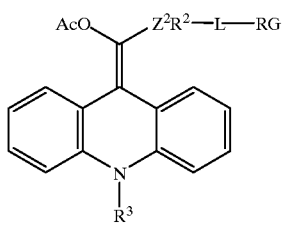
IX

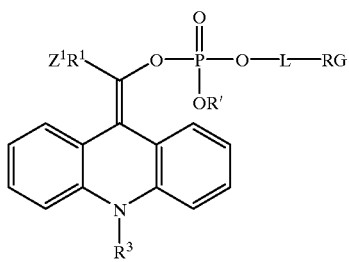
X wherein R" and R' are selected from hydrogen, alkyl, cyanoethyl and alkali metal ions, preferred reactive groups RG include hydroxy, carboxy, amino (NH$_2$), maleimide, NHS esters and trifluoroethanesulfonate (CF$_3$CH$_2$SO$_3$) groups and wherein AcO represents an acetoxy group.

In another aspect, the invention relates to chemiluminescent labeled compounds. By this is meant conjugates of a compound which is to be detected and a chemiluminescent labeling compound of formula I bearing a labeling substituent. When preparing a conjugate using a labeling compound of formula V:

V 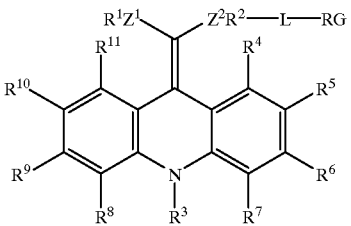

the compound to be labeled with the chemiluminescent label will become attached by means of the reactive group RG of V. The attachement may result in the displacement of a portion of the reactive group RG. For example when an N-hydroxysuccinimide ester is RG, the N-hydroxysuccinimide portion is lost in forming the link. In other cases, RG is intact as for example when it is a maleimide group reacting with an —SH group on a compound being labeled or an isocyanate reacting with an amine or —OH group. In still other cases, the entire RG is lost in forming the link; an example would be when RG is a leaving group such as a halide, azide, N$_3$ or p-toluenesulfonate.

When preparing the chemiluminescent labeled compound, a molar excess of the chemiluminescent labeling compound is typically used although it is not necessary. The chemiluminescent labeling compound is preferably used in at least 5-fold molar excess to the compound to be labeled and usually in at least a 1-fold molar ratio. The chemiluminescent labeled compound may be labeled with one labeling group or multiple copies of the group. In general it is desirable to incorporate multiple labels to increase the amount of signal which can be generated.

Synthetic Methods. Compounds of formula I can be prepared by various methods. In a preferred method, when the Z$^1$ group is O and Z$^2$ is O, S or NR$^{12}$, compound I can be prepared by reacting the enolate of an ester, thioester or amide with a reagent of the formula Z$^1$—LG where LG represents a leaving group as exemplified by the scheme below.

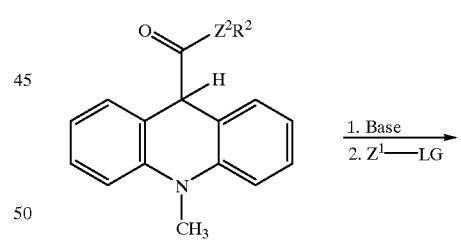

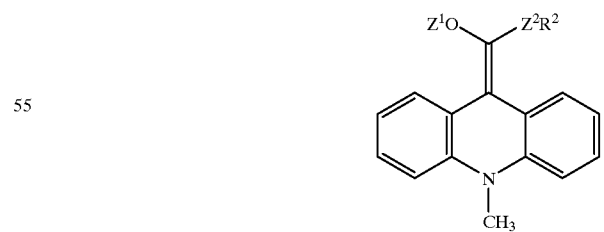

Typical leaving groups include halogens, such as chloride, bromide and iodide, sulfonates such as methanesulfonate and p-toluenesulfonate and trifluoromethanesulfonate, carboxylates such as acetate and benzoate particularly when Z$^1$ is an acyl group in which case Z$^1$—LG would be an acid anhydride, sulfates such as methosulfate, and other groups such as imidazole, triazole and tetrazole, maleimide, succinimidoxy groups.

Methods of preparing compounds of formula I where both Z groups are S atoms include nucleophilic addition of a lithiosilane compound or a phosphorus ylide to a suitable carbonyl compound according to the two schemes below (F. A. Carey, A. S. Court, J. Org. Chem., 37, 1926–29, (1972)).

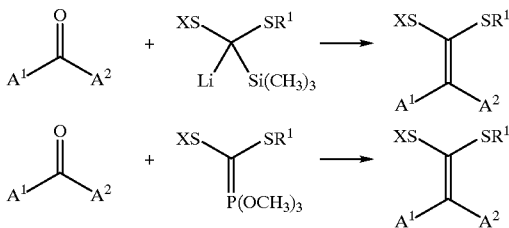

In another method, an ester is converted to a ketene-dithioacetal by reaction with a bis(dialkylaluminum)dithiol reagent as disclosed in E. J. Corey and A. P. Kozikowski, Tetrahedron Lett., 925–8 (1975) and shown below.

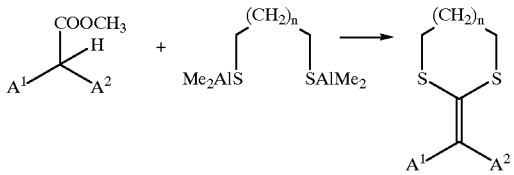

In yet another method, an anion of an active methylene group is reacted with $CS_2$ and the dithiocarboxylate is reacted with a reagent $R_1$—LG containing the $R_1$ group to form a dithioester. An example of the latter methodology is disclosed in I. Shahak and Y. Sasson, Tetrahedron Lett., 4207–10 (1973). The dithioester is converted to the enolate and reacted with a reagent of the formula X—LG.

Methods of preparing chemiluminescent labeling compounds generally involve preparing a precursor compound of formula I and subjecting it to one or more additional reactions, generally known to the skilled artisan, to provide a labeling substituent appended to one of the groups $R^1$ to $R^{11}$, preferably $R^1$ or $R^2$. Numerous examples are provided below to illustrate the general principle.

Analytes. Substances which can be assayed by employing the the present chemiluminescent methods in an assay procedure include various classes of organic and biological molecules. Such assays will generally involve the use of a specific binding reaction between at least one pair of specific binding partners. At least one of the specific binding partners is associated with a compound of formula I in the manner described above. Exemplary analytes include drugs, hormones, pesticides, pesticide metabolites, DNA, RNA, oligonucleotides, antibodies, antibody fragments, antibody-DNA chimeras, antigens, haptens, proteins, carbohydrates, lectins, receptors, avidin, streptavidin and biotin. Exemplary binding partners include antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

The chemiluminescent reactions of the present invention can also be used in a method for detecting hydrogen peroxide, since peroxide can function as the oxidant. It will be apparent to those skilled in the art that the present methods can further be used to detect oxidase enzymes and dehydrogenase enzymes which generate $H_2O_2$ through reduction of oxygen and oxidation of their native substrates. Further the oxidase or dehydrogenase enzyme can be present as a conjugate to a biological molecule or a specific binding pair member in an assay for an analyte.

Assays. In assays conducted by the methods of the present invention, a chemiluminescent compound is associated with the analyte or one member of a specific binding pair. The association can take the form of covalent attachment if the compound possesses a labeling substituent. An example is a chemiluminescent immunoassay. Such assays are commonly used in manual format as well as on automated multi-test immunoassay systems. The speed of generating chemiluminescence achieved by reactions of the present invention is particularly beneficial in adapting it for use with high volume rapid testing instrumentation.

In a typical immunoassay, the analyte hapten, antigen or antibody is assayed by detecting the presence or amount of a chemiluminescent-labeled specific binding partner for the analyte or a labeled analog of the analyte. Various assay formats and the protocols for performing the immunochemical steps are well known in the art. These assays fall broadly into two categories. Competitive assays feature an immunological binding of a specific antibody with the analyte and an analyte analog, e.g. a detectably labeled analyte molecule. Sandwich assays result by the sequential or simultaneous binding of two antibodies, one of which is detectably labeled, with the analyte. The detectably labeled binding pair so formed can be assayed with the compounds and methods of the present invention. Measurement can be performed with labeled species attached to a solid surface or support including beads, tubes, microwells, magnetic particles, latex particles, silica particles, test strips, membranes and filters such as are in common use in the art.

Light emitted by the present method can be detected by any suitable mean, including luminometers, x-ray film, high speed photographic film, a CCD camera or visually. Choice of the detection device will be governed by the application and considerations of cost, convenience, spectral sensitivity and need for a permanent record.

A particularly useful application of the present detection methods is the detection of nucleic acids by the use of labeled nucleic acid probes. Methods for analysis and chemiluminescent detection of nucleic acids using labeled probes, for example, solution hybridization assays, DNA detection in Southern blotting, RNA by Northern blotting, DNA sequencing, DNA fingerprinting, colony hybridizations and plaque lifts are all well established techniques. The label can be present as a direct conjugate with a probe oligonucleotide or capture oligonucleotide or it can be incorporated through indirect linking means using art-known methods. Examples of indirect linking means include using hapten-labeled oligonucleotides and anti-hapten-HRP conjugates or biotinylated oligonucleotides and avidin-HRP conjugates. Such nucleic acid assays can be performed on a blotting membrane or in solution using oligonucleotides attached to solid surfaces including beads, tubes, microwells, magnetic particles or test strips as are known in the art.

Use of the present chemiluminescent reaction for detection of labeled analytes, such as nucleic acids, proteins or antibodies, provides an unexpected advantage over other chemiluminescent labeling methods. It has been found unexpectedly that the chemiluminescent-labeled analyte can undergo electrophoresis and be directly detected in gels such as acrylamide and agarose. Surprisingly, the labeled analyte is not destroyed or triggered at the electrical potential and currents employed in the process as would be expected based on the prior art. Chemiluminescent detection of labeled, electrophoretically separated analytes in the gel has not previously been successful to the best of applicant's knowledge; detection of the separated analytes by chemiluminescence has required transfer of unlabeled analytes to blotting membranes and detection on the membrane by indirect means. The present chemiluminescent detection methods provide adequate intensity when triggering in the gel and thus eliminate the need for a blotting step and binding reactions. This new technique, which represents a significant advance in detection methodology by removing the need for a membrane transfer step, should be particularly well suited for detection of DNA sequencing ladders.

Another exemplary use is the immunological detection of proteins in gels or by the technique of Western blotting. A sample containing a protein of interest as the analyte is subject to electrophoretic separation. The separated proteins are either detected directly in the gel or transferred to a blotting membrane such as a nitrocellulose or PVDF membrane by capillary action or with the aid of an electric field. Transferred protein is detected with a specific primary antibody and a labeled secondary antibody which recognizes and binds to the primary antibody. Quantitative determination of the label reflects the presence of the analyte protein. To adapt the methods of the present invention for Western blotting, secondary antibody is labeled with a chemiluminescent labeling compound of the present invention. Variations on this technique such as using biotinylated antibodies and chemiluminescent labeled avidin are considered within the scope of the invention.

Multi-analyte assays can be performed using two or more distinguishable chemiluminescent labels concurrently to label different analytes. Appropriately chosen chemiluminescent labels may be independently detected on the basis of different emission wavelengths. Alternatively two or more different labels may be distinguishable by the time required to emit the light. Methods for chemiluminescent multi-analyte assays are disclosed in U.S. Pat. No. 5,656,207 the disclosure of which is incorporated herein by reference. Multi-analyte assays can also include detecting multiple regions of the same analyte, such as two different regions of a nucleic acid or two epitopes of an antigen. This type of assay is useful, for example, for detecting gene juxtapositions or for providing increased specificity of detection.

The use of surfactants as additives in the present chemiluminescent reactions is advantageous and can lead to an improvement in analytical sensitivity. Nonionic surfactants useful in the practice of the present invention include by way of example polyoxyethylenated alkylphenols, polyoxyethylenated alcohols, polyoxyethylenated ethers and polyoxyethylenated sorbitol esters. Cationic surfactants, including quaternary ammonium salt compounds such as CTAB, are advantageous for use in increasing the level of chemiluminescence emitted.

In a further embodiment, fluorescent energy acceptors can be employed to shift the maximum emission to longer wavelengths (red-shifting) and/or to increase the quantity of luminescence emitted. Fluorescers can be covalently linked to a compound of formula I or, alternatively, can be added to the reaction solution as separate species, or linked to a polymer or electrostatically associated with a micelle or polymer.

EXAMPLES

1. Synthesis of Acridan Phosphate Compounds. The preparation of compounds 1–13 (Y=Na) and 1a–13a (Y=CH$_2$CH$_2$CN) below was described in Applicant's PCT application WO97/26245.

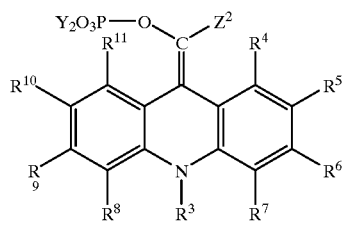

| Compound | $R^3$ | $R^4$–$R^{11}$ | Z | $R^2$ |
|---|---|---|---|---|
| 1 | CH$_3$ | all H | O | phenyl |
| 2 | CH$_3$ | all H | O | 3,5-difluorophenyl |
| 3 | CH$_3$ | $R^6$ = OCH$_3$ | O | phenyl |
| 4 | CH$_3$ | $R^6$ = Cl | O | 2,6-dimethylphenyl |
| 5 | CH$_3$ | all H | S | phenyl |
| 6 | CH$_3$ | $R^8$–$R^9$ = (benzo) | O | phenyl |
| 7 | CH$_3$ | all H | S | 4-fluorophenyl |
| 8 | CH$_3$ | all H | S | 4-methoxyphenyl |
| 9 | CH$_3$ | all H | S | 2,6-dimethylphenyl |
| 10 | CH$_3$ | $R^5$, $R^{10}$ = F | S | phenyl |
| 11 | CH$_3$ | all H | S | trifluoroethyl |
| 12 | CH$_3$ | all H | S | 4-chlorophenyl |
| 13 | CH$_3$ | all H | S | 2-naphthyl |

$R^4$–$R^{11}$ are H unless otherwise indicated.

2. Synthesis of Acridan Derivative 14.

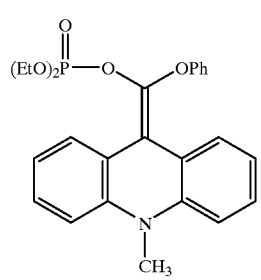

14

A solution of phenyl 10-methylacridan-9-carboxylate (250 mg, 0.79 mmol) in THF was deprotonated with LDA at −78° C. Simultaneously, (EtO)$_2$POCl (205 mg, 1.2 mmol) and pyridine (94 mg, 1.2 mmol) were added via syringes and stirring continued for 15 min. The dry ice bath was removed and stirring continued for 2 h. The volatiles were removed and the product isolated from the residue chromatographically in two steps. A column chromatographic purification using 30% ethyl acetate/hexane allowed separation of the product containing a fluorescent impurity. Final purification was effected by prep. TLC using 10% ethyl acetate/CH$_2$Cl$_2$; $^1$H NMR (acetone-d$_6$) δ 1.08 (t, 6H), 3.46 (s, 3H), 3.76–3.97 (m, 4H), 6.79–7.91 (m, 13H).

3. Synthesis of Acridan Derivative 15.

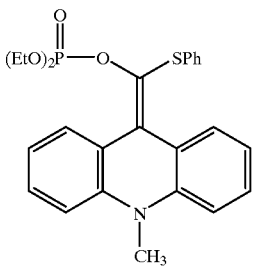

15

A solution of phenyl 10-methylacridan-9-thiocarboxylate (1.0 g, 3 mmol) in THF was deprotonated with LDA at −78° C. Simultaneously, (EtO)$_2$POCl (958 mg, 5 mmol) and pyridine (2.5 mL, 3 mmol) were added via syringes and stirring continued for 15 min. The dry ice bath was removed and stirring continued for 2 h. The volatiles were removed and the product isolated from the residue chromatographically in two steps. A column chromatographic purification using 30–100% ethyl acetate/hexane allowed separation of the product containing blue and green fluorescent impurities. Final purification was effected by prep. TLC using 12% ethyl acetate/CH$_2$Cl$_2$; H NMR (acetone-d$_6$) δ 1.01 (t, 6H), 3.49 (s, 3H), 3.74–3.96 (m, 4H), 6.91–7.45 (m, 11H), 7.78 (d, 1H), 7.99 (d, 1H)

4. Synthesis of Acridan Derivative 16.

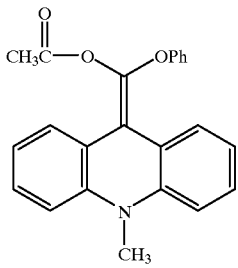

16

A solution of phenyl 10-methylacridan-9-carboxylate (311 mg, 1 mmol) in THF was added dropwise to a solution of LDA at −78° C. After minutes at −78°0 C., acetic anhydride (161.3 mg, 1.6 mmol) was added via syringe and the dry ice bath was removed. After one hour, the volatiles were removed and the product isolated from the residue chromatographically. A column chromatographic purification using 5% ethyl acetate/hexane provided a 90 mg pure fraction as a white solid and a second fraction (250 mg) which contained some starting material; $^1$H NMR (CDCl$_3$) δ 2.04 (s, 3H), 3.44 (s, 3H), 6.82–7.65 (m, 13H).

5. Synthesis of Acridan Derivative 17.

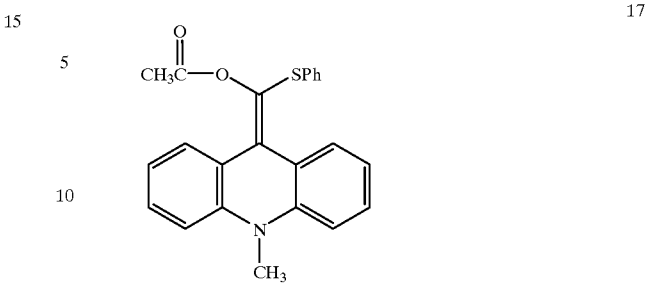

17

A solution of phenyl 10-methylacridan-9-thiocarboxylate (1.05 g) in THF was deprotonated with LDA at −78° C. Acetic anhydride (0.45 mL) in 10 mL of THF was added dropwise, the dry ice bath was removed and continued stirring over night. The volatiles were removed and the product isolated from the residue chromatographically. A column chromatographic purification using 5–20% ethyl acetate/hexane provided 1.15 g of compound 40 as an off-white solid; $^1$H NMR (CDCl$_3$) δ 1.89 (s, 3H), 3.48 (s, 3H), 6.95–7.06 (m, 4H), 7.20–7.34 (m, 5H), 7.40–7.44 (m, 2H), 7.62 (d, 1H), 7.79 (d, 1H).

6. Synthesis of Acridan Derivative 18.

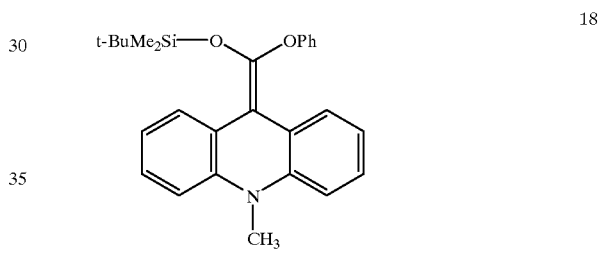

18

A solution of phenyl 10-methylacridan-9-carboxylate (333.4 mg, 1.06 mmol) in THF was deprotonated with LDA at −78° C. for 30 min. The deep orange solution was treated with t-butyldimethylsilyl chloride (253.4 mg, 1.68 mmol) in 10 mL of dry THF. The dry ice bath was removed and stirring continued for 2 h. The volatiles were removed and the product isolated as an oil (212 mg) from the residue chromatographically using 5% ethyl acetate/hexane; $^1$H NMR (CDCl$_3$) δ −0.12 (s, 6H), 0.77 (s, 9H), 3.37 (s, 3H), 6.75–7.38 (m, 12H), 7.79 (dd, 1H).

7. Synthesis of Acridan Derivative 19.

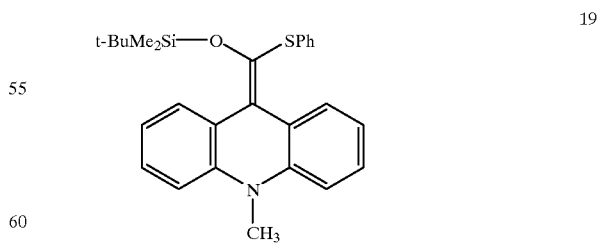

19

A solution of phenyl 10-methylacridan-9-thiocarboxylate (322.3 mg, 0.97 mmol) in THF was deprotonated with LDA at −78° C. t-Butyldimethylsilyl chloride (270 mg, 1.8 mmol)

in 5 mL of dry THF was added rapidly, the dry ice bath was removed and stirring continued for 90 min. The volatiles were removed and 330 mg of the product isolated from the residue chromatographically using 5% ethyl acetate/hexane as an oil which solidified on standing; $^1$H NMR (CDCl$_3$) δ −0.09 (s, 6H), 0.73 (s, 9H), 3.43 (s, 3H), 6.84–7.01 (m, 4H), 7.16–7.47 (m, 7H), 7.73–7.76 (m, 1H), 7.90–7.93 (m, 1H).

8. Synthesis of Acridan Derivative 20.

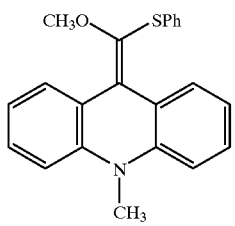

20

Phenyl 10-methylacridan-9-thiocarboxylate, 1.0 g was converted to the enolate with LDA in 60 mL of dry THF at −70° C. After maintaining the temperature at —70° C. for 1 h, 0.76 g of methyl triflate was added and the reaction mixture was allowed to warm to room temperature. The mixture was allowed to stand for 4 days. CH$_2$Cl$_2$ (150 mL) was added, the solution was extracted with water and dried on Na$_2$SO$_4$. The crude product was purified by prep. TLC with a 70/30 hexane:CH$_2$Cl$_2$ eluent. $^1$H NMR (CDCl$_3$) δ 3.53 (s, 3H), 3.56 (s, 3H), 6.93–7.45 (m, 11H), 7.71 (d, 1H), 7.93 (d, 1H).

9. Synthesis of Acridan Derivative 21.

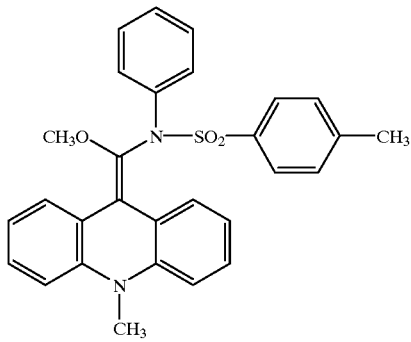

21

10-Methyl—N-(phenyl)—N-(p-toluenesulfonamido) acridan-9-carboxamide was prepared as described in U.S. Pat. No. 5,491,072. The sulfonamide is converted to the enolate with LDA in dry THF and methylated using methyl triflate to produce compound 21.

10. Synthesis of Acridan Derivative 22.

a) Acridine-9-carboxylic acid chloride (4.0 g) was esterified with 4-hydroxythiophenol (2.8 g) in a solution of pyridine (2.94 mL) and CH$_2$Cl$_2$ (25 mL) over night at room temperature. The mixture was filtered and the filtrate evaporated to dryness. The residue was combined with the precipitate from the reaction and washed with water and CH$_2$Cl$_2$ to remove impurities, yielding 3.8 g (70%) of the thioester.

b) the thioester (2.0 g) was reduced with zinc (3.9 g) and acetic acid in CH$_2$C$_2$ under an atmosphere of argon for 3 h at room temperature. The insoluble product was filtered, washed with CH$_2$Cl$_2$, dissolved in acetone to separate it from the inorganics and evaporated, yielding 1.7 g (85%) of the acridan thioester.

c) The acridan thioester was methylated on nitrogen with methyl triflate (3.3 g) in CH$_2$Cl$_2$ over night at room temperature. Evaporation to dryness,partition between CH$_2$Cl$_2$ and water, and drying left a crude product which was purified by column chromatography with 30% ethyl acetate/hexane, yielding 1.55 g (88%) of the N-methylated thioester.

d) The phenolic group was protected as the TMS ether by reacting 2 g of the thioester with 1.25 g of trimethylsilyl chloride in 20 mL of THF containing 0.91 g of pyridine over night at room temperature. The reaction mixture was filtered and the filtrate evaporated to dryness. The crude product was purified by column chromatography with 25% ethyl acetate/hexane.

e) The thioester was converted to the enol bis(cyanoethyl) phosphate with concomitant removal of the silyl protecting group. The thioester enolate, generated by reaction of 2 g of the thioester with LDA in THF at −78° C. was further reacted with POCl$_3$ (0.87 g) and pyridine (0.45 g) in THF. After 1 hour at room temperature 3-hydroxypropio-nitrile (1.56 g) was added as a pyridine solution and the mixture stirred over night. The reaction mixture was filtered, evaporated and applied to a column for purification with ethyl acetate, yielding a slightly impure product. The product was further washed with water to remove residual 3-hydroxypropionitrile, dried and evaporated yielding 0.92 g of product. $^1$H NMR (CDCl$_3$) δ 2.55 (m, 4H), 3.50 (s, 3H), 3.94 (m, 2H), 4.06 (m, 2H), 5.94 (s, 1H), 6.85 (d, 2H), 7.06 (m, 4H), 7.33 (m, 4H), 7.87 (dd, 2H).

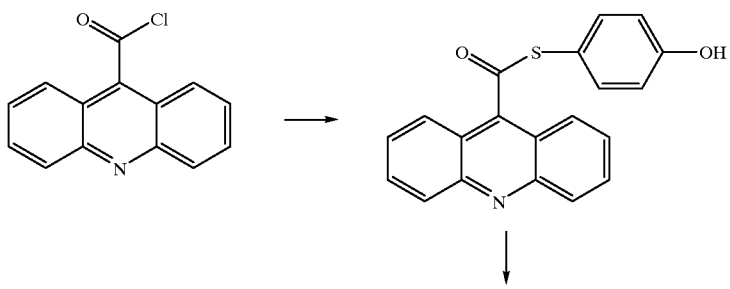

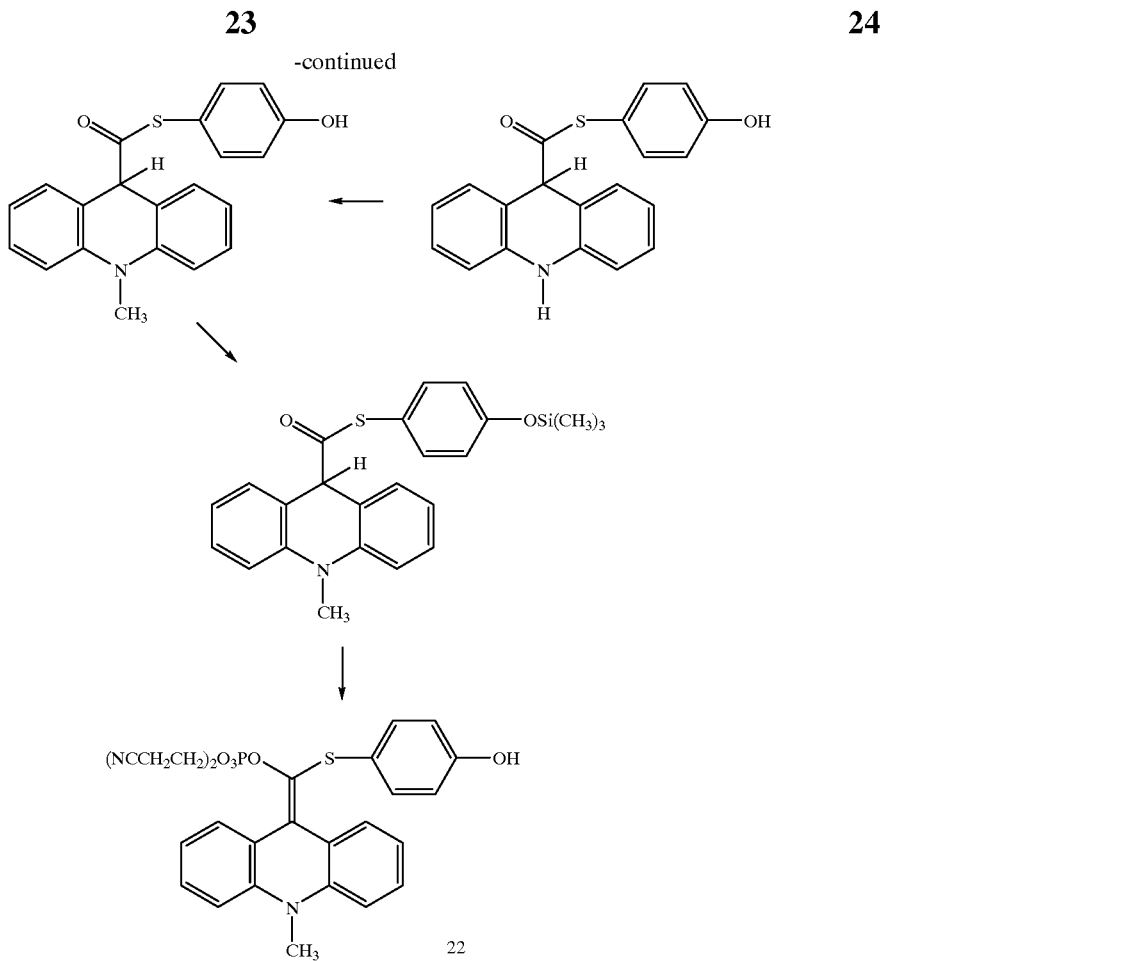

11. Synthesis of Acridan Derivative 23.

a) 6-Aminohexanol (0.5 g) was silylated with 0.556 g of trimethylsilyl chloride and 0.72 mL of triethylamine in 20 mL of THF over night. The mixture was filtered and the residue evaporated to dryness. The Silyl ether was converted to the phenyl carbamate by reacting with phenyl chloroformate (0.735 g) and 1 mL of pyridine in $CH_2Cl_2$. The solution was diluted into $CH_2Cl_2$, washed with water and dried. The silyl ether group was cleaved with dilute HCl in THF. The product A was isolated by column chromatography.

b) Compound 22 was treated with $POCl_3$ and pyridine to phosphorylate the phenol. Reaction with compound A (below) for 3.5 h at room temperature in $CH_2Cl_2$, partitioning the reaction mixture between $CH_2Cl_2$ and water, drying and chromatography with 20–50% methanol/$CH_2Cl_2$ yielded compound 23. $^1H$ NMR ($CDCl_3$) δ 1.17–1.48 (m, 8H), 2.40–2.44 (m, 4H), 3.01–3.04 (m, 2H), 3.45 (s, 3H), 3.82–3.96 (m, 6H), 5.60 (bt, 1H), 6.89–7.29 (m, 15H), 7.76–7.84 (m, 2H).

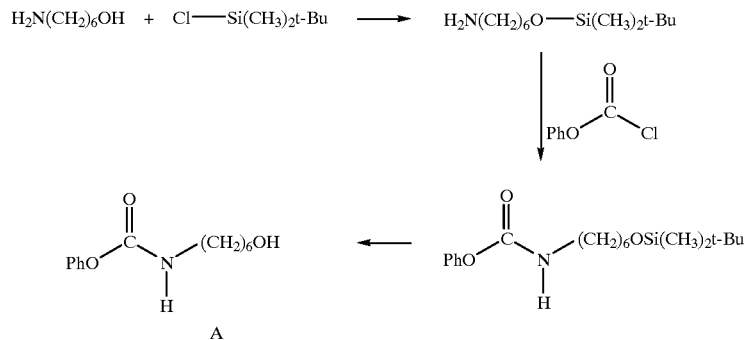

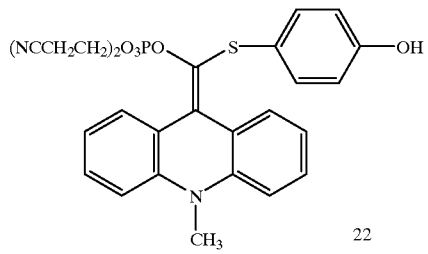

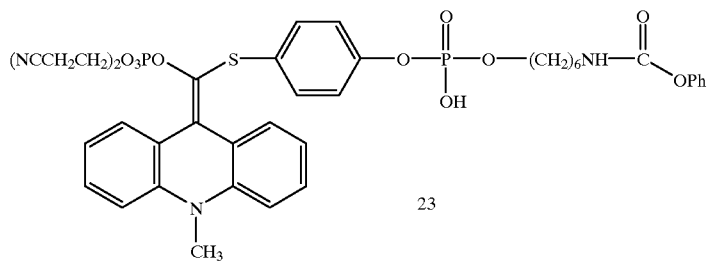

12. Synthesis of Acridan Derivative 24.

a) Compound 23 (90 mg) was hydrolyzed in aqueous NaOH/acetone by stirring a solution for 1 day at room temperature to remove the carbamate and cyanoethyl groups. The solution was evaporated and the gummy solid triturated with methanol to crystallize the product, yielding 64 mg. $^1$H NMR (D$_2$O) δ 1.01–1.46 (m, 8H), 2.46–2.90 (2t, 2H), 3.33 (s, 3H), 3.77–3.83 (m, 2H), 6.89–7.3 (m, 10H), 7.80–7.83 (d, 1H), 8.14–8.17 (d, 1H).

13. Synthesis of Acridan Derivative 25.

a) Compound 24 (15 mg) was dissolved in 800 μL of D$_2$O and added to a solution of 6-maleimidohexanoic acid NHS ester (8.4 mg) in 75 μL of p-dioxane-d$_8$ in a micro-centrifuge tube. The tube was vortexed briefly to mix. The solution was diluted with methanol and evaporated to dryness. The orange solid was crystallized from methanol/acetone, washed with acetone and dried, yielding 17 mg of light orange solid. $^1$H NMR (CD$_3$OD) δ 1.25–1.58 (m, 14H), 2.11 (t, 2H), 3.09 (t, 2H), 3.33 (s, 3H), 3.45 (t, 2H), 3.83–3.85 (m, 2H), 6.76–7.16 (m, 12H), 7.87–7.89 (d, 1H), 8.44–8.46 (d, 1H).

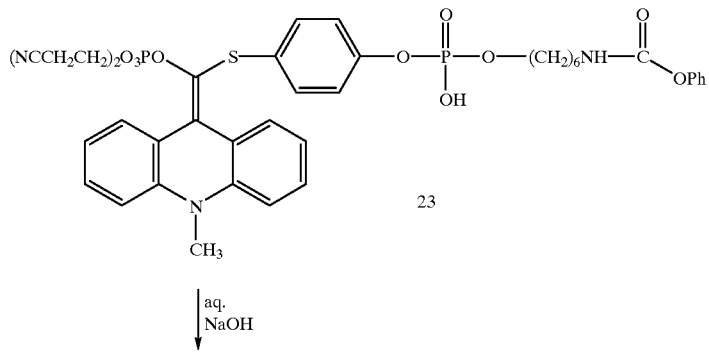

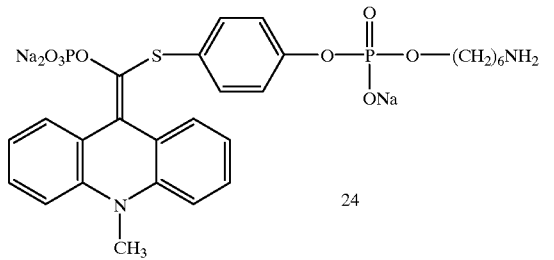

24

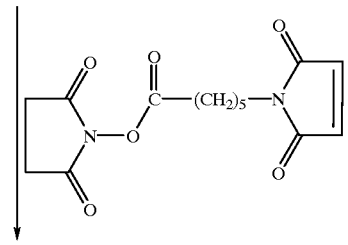

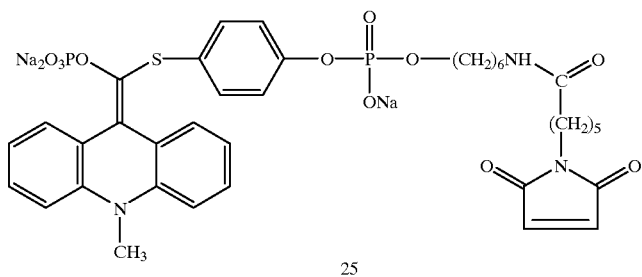

25

14. Synthesis of Acridan Derivative 26.

a) A solution of 6-maleimidohexanoic acid NHS ester (22.7 mg) in THF was reacted with 6-aminohexanol. After min, the solution was centrifuged and the liquid decanted. The solid was washed with THF, the supernatants being combined. The THF was evaporated and the residue partitioned between $CH_2Cl_2$ and water. Drying and evaporating the organic layer yielded compound B.

b) Compound 22 (57 mg) was phosphorylated in a solution of POCl3 (18 mg), pyridine (168 mg) and 1.5 mL of $CH_2Cl_2$ at 0° C. After ca. 90 min, a solution of B (40 mg) in 2.5 mL of $CH_2Cl_2$ was added at 0° C and the mixture stirred for 4.5 h. The mixture was diluted with $CH_2Cl_2$, washed with water, dried and concentrated. Compound 26 was isolated from the crude product by prep. TLC. $^1$H NMR ($CDCl_3$) δ 1.18–1.53 (m, 14 H), 2.03 (t, 2H), 2.28 (bs, 1H), 2.51 (m, 4H), 3.04–3.05 (m, 2H), 3.42 (t, 2H), 3.48 (s, 3H), 3.89–3.97 (m, 6H), 6.28 (bs, 1H), 6.62 (s, 2H) 6.89–7.34 (m, 10H), 7.75–7.78 (d, 1H), 7.81–7.84 (d, 1H).

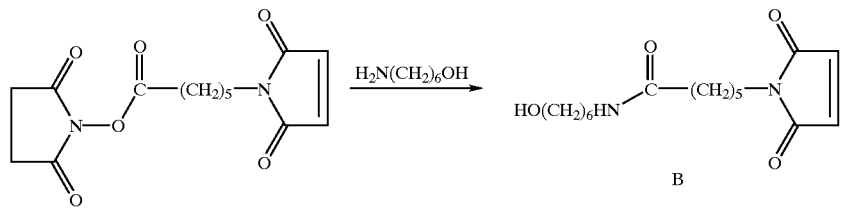

B

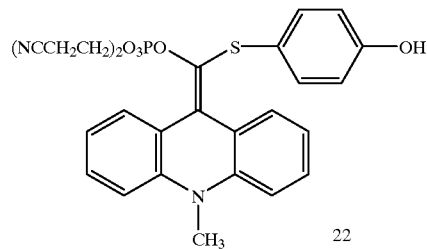

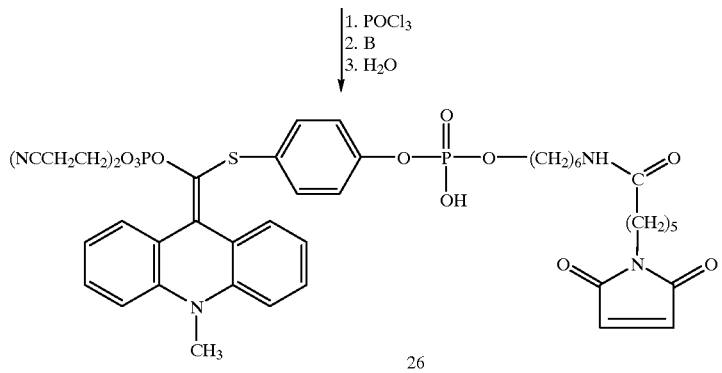

15. Synthesis of Acridan Derivative 27.

a) Compound 22 (0.2 g) was reacted with 93 mg of AgO and 0.2 g of NHS iodoacetate in acetonitrile for 1 h at room temperature under a blanket of argon. The mixture was filtered, the solid washed with acetone and the combined organic solutions evaporated. The coupled product was purified from the crude by chromatography using 50–75% ethyl acetate/hexane, yielding 64 mg of Compound 27. $^1$H NMR (CDCl$_3$) δ 2.48–2.55 (m, 4H), 2.77 (s, 4H), 3.53 (s, 3H), 3.88–4.00 (m, 4H), 4.97 (s, 2H), 6.99–7.94 (m, 12H).

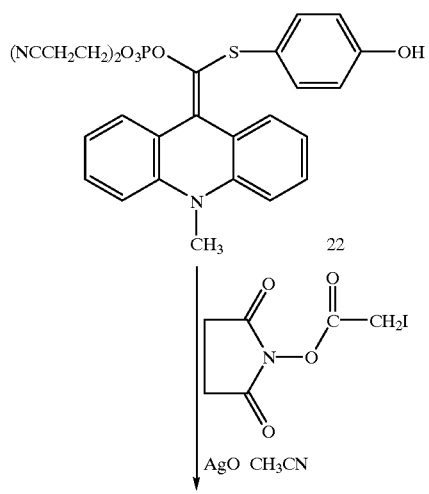

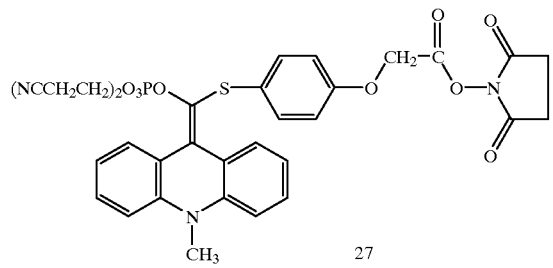

16. Synthesis of Acridan Derivative 28.

a) A solution of 3-mercaptopropanoic acid (118 mg), N-hydroxysuccinimide (192 mg) and DCC (252 mg) in DMF was stirred under argon. After 45 min, the precipitate was filtered and washed with THF. The solid was suspended in acetone and the acetone solution applied to a prep. TLC plate for chromatographic purification using 40% ethyl acetate/hexane. The coupled product C was isolated as an oil (90 mg).

b) Compound 25 (2.5 mg) was dissolved 1 mL of in 1:1 methanol/phosphate buffer, pH 6.0 and then evaporated to dryness to convert the disodium phosphate group to the monoacid form. This compound and Compound C were dissolved together in DMF-d$_6$ and maintained for 10 min. The DMF was removed under vacuum.

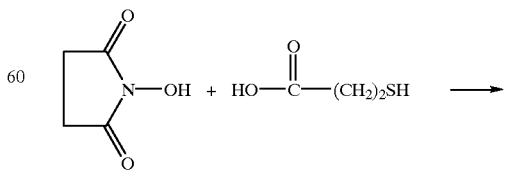

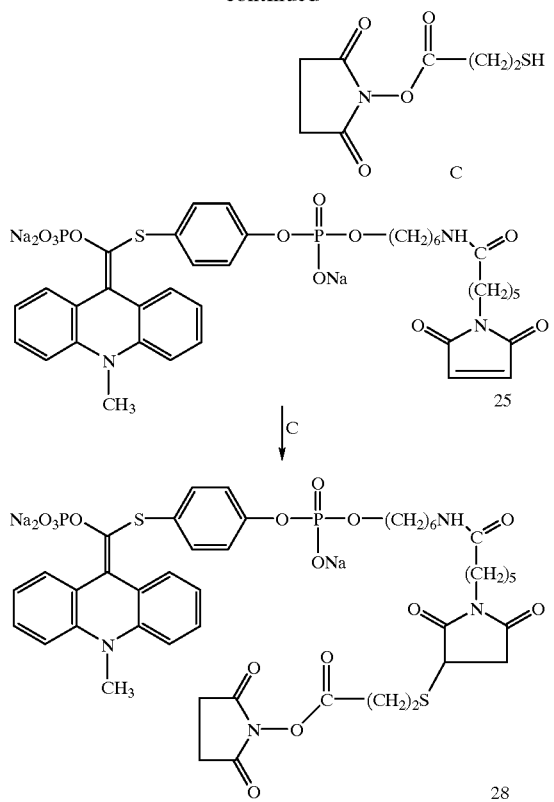

17. Synthesis of Acridan Derivative 29.

a) The silyl-protected thioester intermediate (below) of Example 13 (prepared from 5 g of the non-silylated precursor) was deprotonated with LDA and phosphorylated with POCl$_3$ using the procedures essentially as described above. Ethanol (4.75 mL) was added to the dichlorophosphate intermediate and stirring continued over 0night. The solid was filtered off and the filtrate evaporated to dryness, leaving an oil. The oil was chromatographed using 30–50% ethyl acetate/hexane yielding 2.37 g of the enol diethyl phosphate intermediate as a slightly yellow solid.

b) The enol diethyl phosphate intermediate (288 mg) was phosphorylated at the phenol group with POCl$_3$/pyridine in CH$_2$Cl$_2$ by stirring for ca. 3 h. Compound A (141 mg) in CH$_2$Cl$_2$ was added and the solution stirred over night at room temperature. The solution was washed with water, dried and concentrated. The residue was separated by prep. TLC, yielding the carbamate-protected intermediate (82 mg).

c) The carbamate-protected intermediate (82 mg) was hydrolyzed in aqueous NaOH/acetone by stirring a solution for 6 h at room temperature under argon to remove the carbamate group. The solution was diluted into methanol/acetone to crystallize the product, yielding a first crop of 21 mg of Compound 23. The filtrate was evaporated and the residue chromatographed (25–50% methanol/CH$_2$ Cl$_2$) to obtain a further 40 mg of product. $^1$H NMR (CDCl$_3$) δ 1.12 (s, 6H), 1.34–1.72 (m, 8H), 2.82 (bt, 2H), 3.46 (s, 3H), 3.74–3.97 (m, 6H), 6.89–7.34 (m, 10H), 7.76–7.78 (d, 2H), 8.25 (5s, 1H).

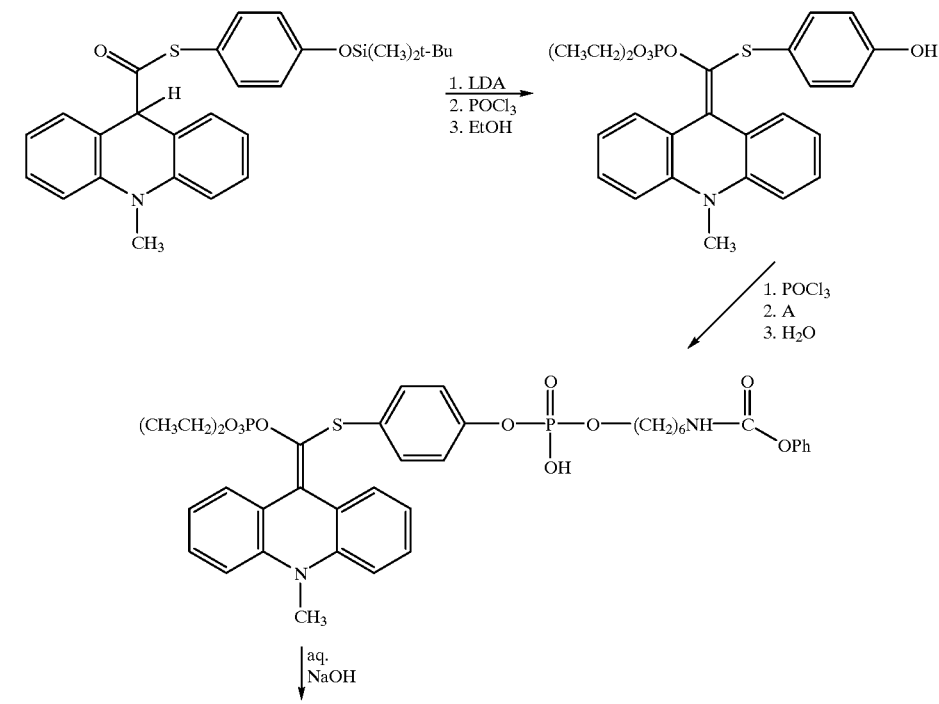

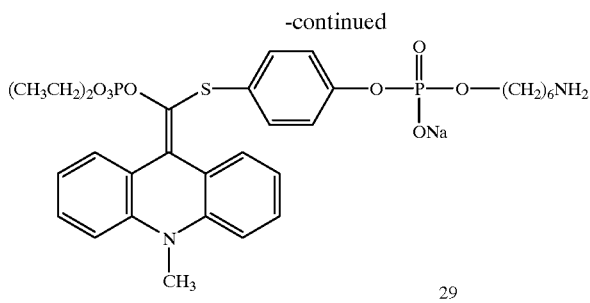

29

18. Synthesis of Acridan Derivative 30.

a) Phenyl 10-methylacridan-9-thiocarboxylate (0.5 g) was deprotonated with LDA in THF at −78° C. and treated with POCl₃/pyridine at −78° C. to room temperature to form the enol dichlorophosphate. A solution of A in THF was added and stirring continued over night. The solution was evaporated and the residue partitioned between ethyl acetate and water. Drying and evaporating the ethyl acetate produced an orange solid which was washed with hexane to remove residual pyridine. The solid was dissolved and subjected to column chromatography using 5–50% methanol/CH₂Cl₂; several fractions containing the desired product along with impurities were combined and evaporated. This material was further purified by prep. TLC with 15% methanol/CH₂Cl₂ to provide the carbamate-protected product pure.

c) The carbamate-protected product was (17 mg) was hydrolyzed in aqueous NaOH/acetone by stirring a solution over night at room temperature under argon to remove the carbamate group. The solution was evaporated and the residue chromatographed (25–50% methanol/CH₂Cl₂) producing 8 mg of Compound 30. ¹H NMR (CDCl₃) δ 1.07–1.33 (m, 8H), 2.39 (t, 2H), 3.34 (s, 3H), 3.40–3.42 (m, 2H), 6.85–7.37 (m, 11H), 7.68–7.70 (d, 1H), 8.12–8.14 (d, 1H).

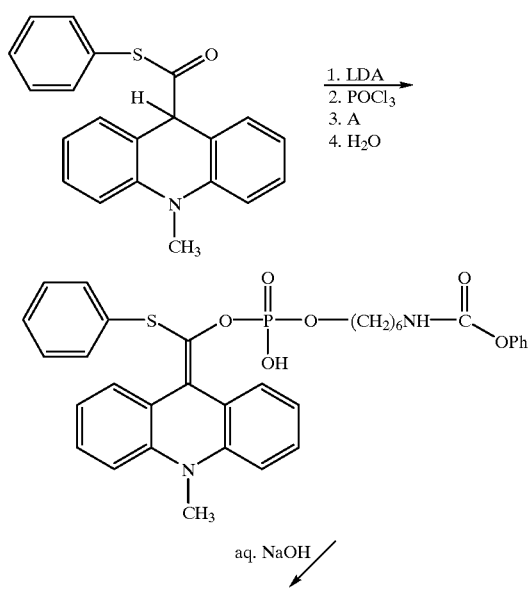

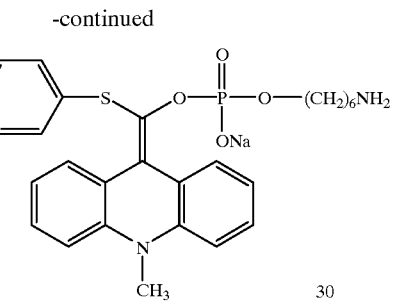

30

19. Synthesis of Acridan Derivative 31.

a) p-Hydroxyphenyl 10-methylacridan-9-carboxylate (preparation described in U.S. Pat. No. 5,491,072) (1.1 g) was silylated with 0.46 mL of chlorotrimethylsilane and 1.02 mL of triethylamine in THF upon stirring over night. The mixture was filtered, and the solution evaporated to dryness.

b) The silyl ether compound of step a was converted to the enolate with LDA in THF at −78° C. After min, a solution of acetic anhydride (0.5 mL) in THF was added dropwise. The reaction was maintained at −78° C. for min and warmed to room temperature. Volatiles were removed and the residue chromatographed using 5–10% ethyl acetate/hexane. A fraction was obtained which contained the desired enol acetate along with the starting p-hydroxyphenyl ester.

c) The mixture of products from step b (100 mg) was reacted with trifluoroethanesulfonyl chloride (72 mg) and pyridine (62 mg) in CH₂Cl₂ at room temperature for 1 h. The mixture was evaporated to dryness and chromatographed using 10–50% CH₂Cl₂/hexane. Compound 31 (70 mg) was separated. ¹H NMR (CDCl₃) δ 2.09 (s, 3H), 3.45 (s, 3H), 3.95–4.03 (q, 2H), 6.85–7.58 (m, 12H).

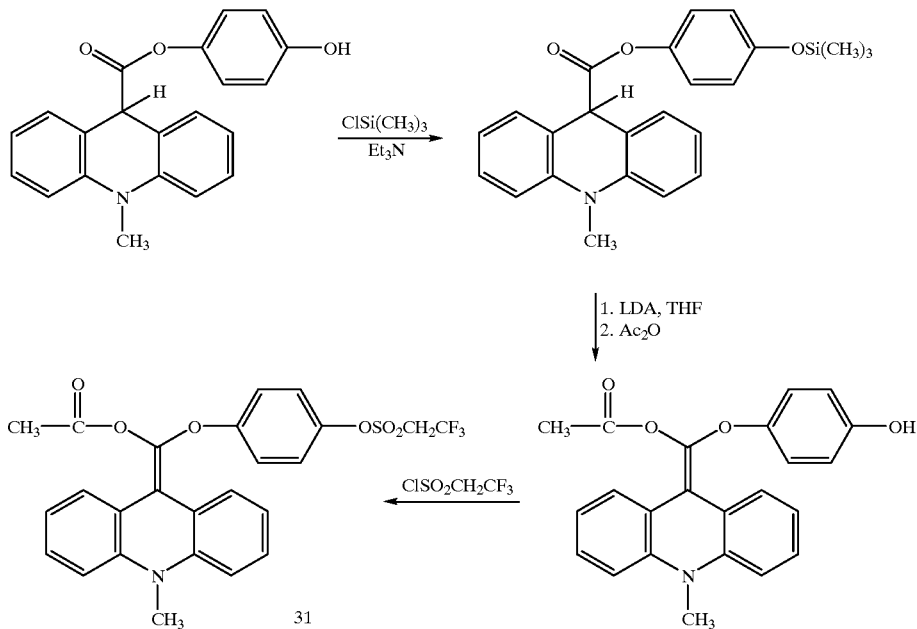

20. Synthesis of Acridan Derivative 32.

a) 3-(p-Hydroxyphenyl)propanoic acid was converted to 3-(p-mercaptophenyl)propanoic acid by adapting the method of Tagawa (H. Tagawa, K. Ueno, Chem. Pharm. Bull., 26(5) 1384–93, 1978)). Briefly, the starting acid was esterified with ethanol, the phenol group, converted to the diethylxanthate, rearranged to the isomeric xanthate, and saponified to generate the mercapto-substituted acid.

b) The methyl ester of this acid was condensed via its —SH group with acridine-9-carboxylic acid chloride. The acridine ring was reduced with zinc/$CH_3COOH$ to the corresponding acridan compound which was methylated on nitrogen with methyl triflate.

c) The thioester was converted to the enol bis(cyanoethyl) phosphate. The thioester enolate, generated by reaction of 1 g of the thioester with LDA in THF at $-78°$ C. was further reacted with $POCl_3$ (0.64 g) and pyridine (1.9 g) in THF. After 1 h at room temperature, 3-hydroxypropionitrile (1.14 mL) in 1 mL of pyridine and the mixture stirred over night. The reaction mixture was filtered, evaporated and applied to a column for purification with ethyl acetate, yielding the bis(cyanoethyl)phosphate.

d) Saponification of the phosphate and carboxylate esters occurred upon reaction in acetone/aq. NaOH at room temperature, yielding compound 32 (100 mg). $^1$H NMR ($D_2O$) δ 2.33 (t, 2H), 2.70 (t, 2H), 3.34 (s, 3H), 6.89–7.34 (m, 10H), 7.70–7.80 (d, 1H), 8.18–8.19 (d, 1H).

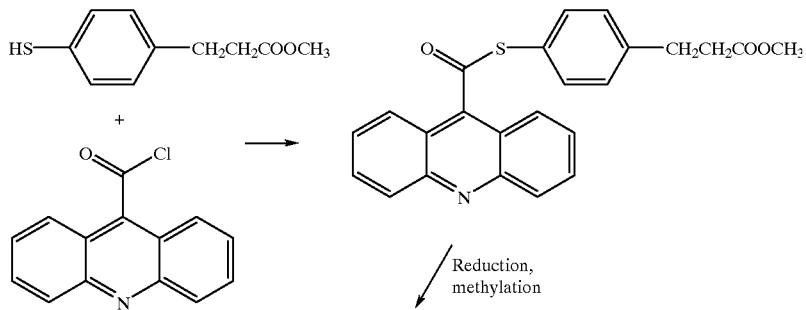

-continued

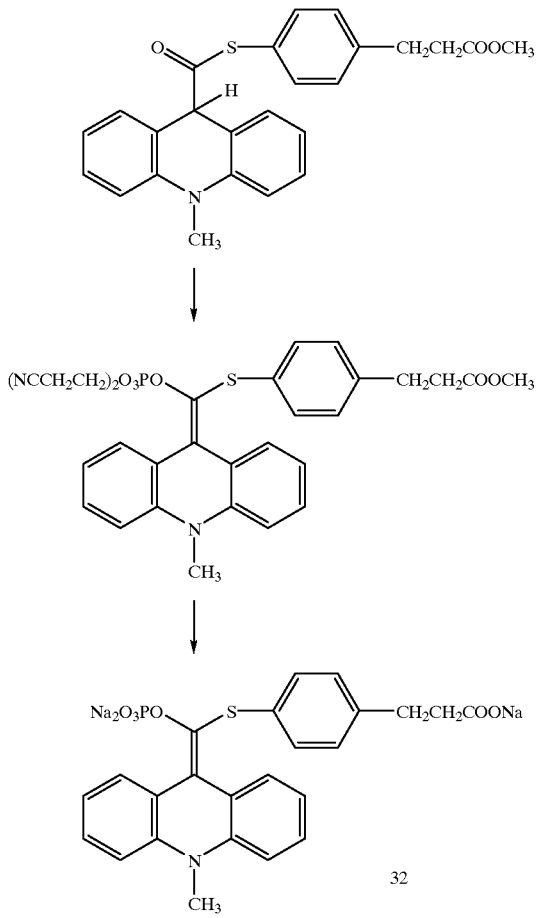

32

Numerous other acridan phosphate labeling compounds can be prepared derived from those described in applicant's PCT Application WO 97/26245 and U.S. application Ser. No. 08/928,793 by providing a labeling substituent.

21. Kinetic Profile of Chemiluminescence Intensity of Acridan Phosphate 5. A reagent comprising $3.3 \times 10^{-4}$M acridan phosphate 5 in 0.1M tris buffer, pH 8.8 (10 μL) was mixed with 50 μL of 3.6% urea peroxide in 0.4M $HNO_3$ and incubated for 2 min. Chemiluminescence was triggered by injecting 100 μL of 0.25M NaOH solution. Light production occurred instantly upon mixing and was integrated for 5 sec. The time course of chemiluminescence emission is depicted in FIG. 1.

22. Use of Different Acids. The ability to use various acidic compounds in the method of generating chemiluminescence from acridans is illustrated in Tables 1 and 2. Acridan phosphate 5 (8 nM or 2 μM) in 0.1M tris buffer, pH 8.8 (10 μL) was mixed with 50 μL of 3.6% urea peroxide in 0.4M solutions of various acids and incubated for 2 min. Chemiluminescence was triggered by injecting 10 μL of 0.25M NaOH solution. As summarized below, each acid was effective in the present method to generate light rapidly. Light intensity values are in arbitrary units. Total intensity was determined over a 10 s period.

TABLE 1

Triggering an 8 nM Solution of Acridan phosphate 5

| Acid | Peak Intensity | Total Intensity |
|---|---|---|
| $HNO_3$ | 79 | 40 |
| HCl | 74 | 37 |
| $H_2SO_4$ | 25 | 13 |

TABLE 2

Triggering a 2 μM Solution of Acridan phosphate 5

| Acid | Peak Intensity | Total Intensity |
|---|---|---|
| $HNO_3$ | 2000 | 1090 |
| HCl | 8700 (ca.) | 4630 |
| $H_2SO_4$ | 616 | 345 |

23. Triggering with Peroxide/Base Solution.

Chemiluminescence was also generated from a compound of the present invention by using a triggering reaction in which the peroxide is in the base solution. A 2 μM solution of acridan phosphate 5 in 0.1M tris buffer, pH 8.8 (10 μL) was mixed with 50 μL of 0.4M acid and incubated for 2 min. Chemiluminescence was initiated by addition of 100 μL of 3.6% urea peroxide in 0.25M NaOH solution. As summarized below, each acid was effective in the present method. Total intensity was measured for 10 s.

TABLE 3

| Acid | Peak Intensity | Total Intensity |
| --- | --- | --- |
| $HNO_3$ | 8500 | 5000 |
| HCl | 2640 | 1700 |
| $H_2SO_4$ | 200 | 100 |

24. Effect of acid incubation time. Solutions of acridan phosphate 5 (1 $\mu$M in 0.4M HCl) were treated as described in Example 22, varying the length of the acid/peroxide incubation step.

TABLE 4

| Incubation Time | Peak Intensity | Total Intensity |
| --- | --- | --- |
| 1 min | 5777 | 3070 |
| 2 | 5501 | 3290 |
| 5 | 4788 | 3900 |
| 10 | 5379 | 4110 |

25. Sensitivity of Detecting Acridan Derivative 5.

Figure 2:
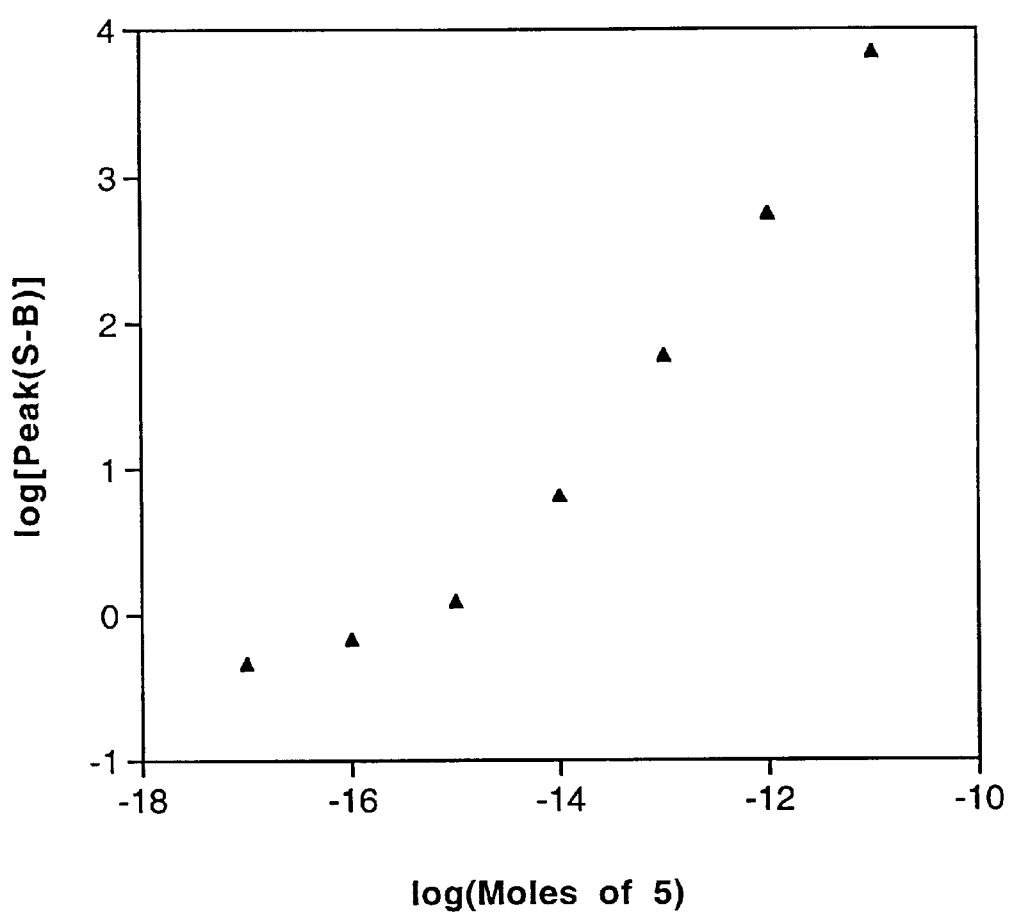
FIG. 2 is a graph relating the amount of compound to the maximum chemiluminescence intensity emitted by acridan phosphate 5 triggered at room temperature. Chemiluminescence emission was initiated by adding 100 μL of a 0.25M NaOH solution.

Solutions of acridan phosphate 5 (10 $\mu$L) containing between $10^{-11}$ and $10^{-17}$ moles were each added to 50 $\mu$L of 3.6% urea peroxide in 0.4M HCl and incubated for 2 min at 25° C. Chemiluminescence was initiated by adding 100 $\mu$L of 0.25M NaOH to each of these solutions. Peak and total light intensity were measured by single determinations. Background light levels were 0.038 (peak) and 0.019 (total) under these conditions. The data are presented in Table 5 and FIG. 2.

TABLE 5

| Moles of 5 | Peak Intensity | Total Intensity |
| --- | --- | --- |
| $10^{-11}$ | 7010 | 3990 |
| $10^{-12}$ | 555 | 380 |
| $10^{-13}$ | 60 | 31.5 |
| $10^{-14}$ | 6.6 | 3.10 |
| $10^{-15}$ | 1.96 | 1.28 |
| $10^{-16}$ | 0.90 | 0.72 |
| $10^{-17}$ | 0.56 | 0.50 |

26. Detection of Various Exemplary Compounds. Each of the compounds in Table 6 was prepared as a 0.5 $\mu$M stock solution. Ten $\mu$L aliquots were separately added to 50 $\mu$L of 3.6% urea peroxide in 0.4M HCl and incubated for 2 min at 25° C. Chemiluminescence was triggered by addition of 100 $\mu$L of 0.25 M NaOH. Chemiluminescence was measured for 10 s. Significant levels were produced with each of the compounds. Compounds 2–4, 6–13, 18–19 and 21–32 also produced chemiluminescence when triggered under the conditions of this example as well as Examples 22 and 23.

TABLE 6

| Compound | Peak Intensity | Total Intensity |
| --- | --- | --- |
| 1 | 687 | 1640 |
| 5 | 2346 | 2000 |
| 5a | 3586 | 2710 |
| 14 | 229 | 707 |
| 15 | 2475 | 1700 |
| 16 | 769 | 1560 |
| 17 | 8331 | 5520 |
| 20 | 632 | 447 |

27. Conjugation of Labeling Compound to Protein. Bovine serum albumin (BSA) (Fluka) was reduced using the Reduce-Imm™ kit (Pierce, Rockford, Ill.) to liberate free sulfhydryl groups according to the manufacturer's instructions.

A fraction containing 270 $\mu$g of BSA in 200 $\mu$L of equilibration buffer #2 from the Reduce-Imm kit was incubated with 50 $\mu$L of a solution of Compound 25 in methanol over night at room temperature. The solution was passed through a Sephadex G-25 column with 0.01 M phosphate, pH 7.5. Fractions were analyzed spectrophotometrically at 280 nm and by a chemiluminescence assay using urea peroxide and $HNO_3$ followed by NaOH as described above. Fractions containing both label and protein were pooled. The product is designated BSA—APNa2.

28. Conjugation of BSA to Acridan Derivative 26. Labeling of reduced BSA with compound 26 was carried out by the method of the previous example using DMF in place of methanol. BSA was thereby labeled with a bis(cyanoethyl) phosphate acridan compound. The product is designated BSA—$APCN_2$.

29. Detection of Chemiluminescent-Labeled BSA. Samples of BSA—$APNa_2$ and BSA—$APCN_2$, were assayed for protein content according to the method described in (Warburg and Christian, B. Z., 310, 384 (1941)). Stock solutions were diluted in Laemmli buffer (U. K. Laemmli, Nature (London), 227, 680 (1970)) and loaded onto 7% acrylamide-bisacrylamide gels. Proteins were subjected to SDS-PAGE at 120–130V for 1–1.5 h at room temperature. The gels were removed and placed into a plastic frame constructed from the side edge of a Petri dish and a transparency film.

Figure 3A:
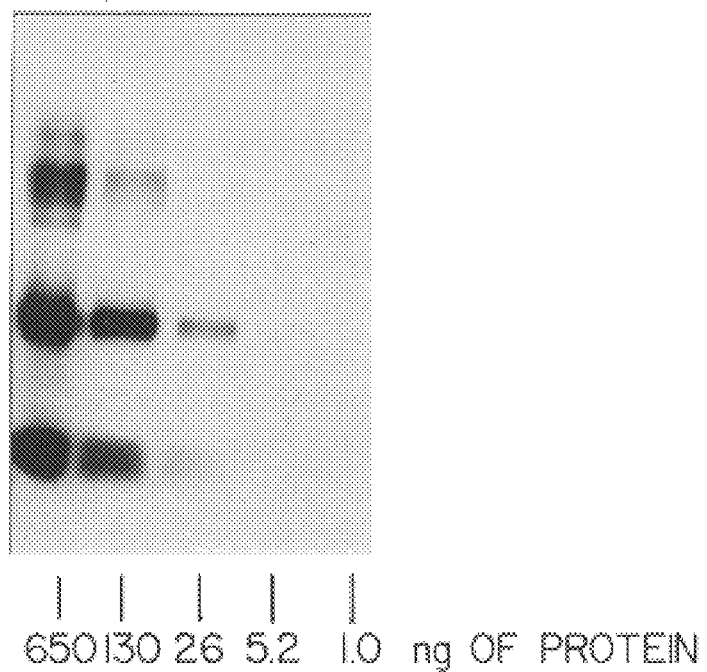
FIGS. 3A and B are images of an x-ray film from the detection of chemiluminescent labeled protein in a polyacrylamide electrophoresis gel by exposing the gel to X-ray film for 20 min as soon as the chemiluminescent reaction began.
Figure 3B:
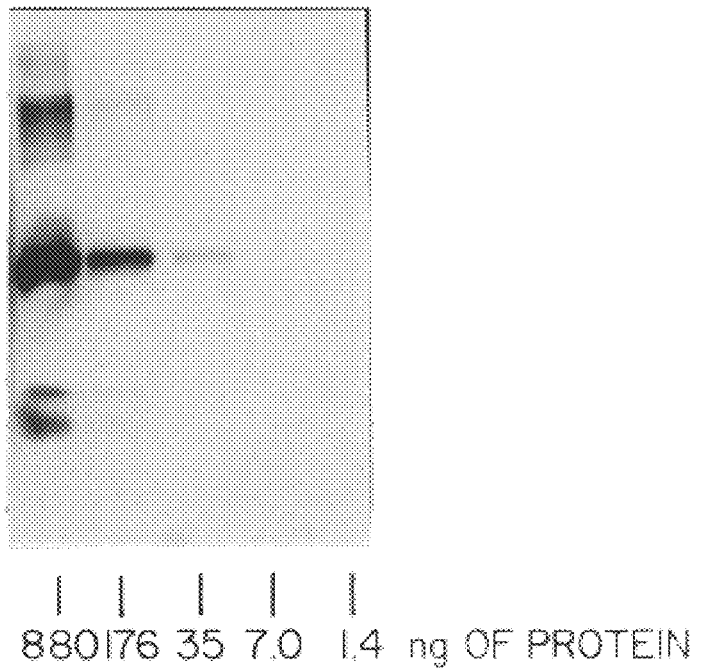
FIG. 3B shows the detection of BSA—$APCN_2$.

Labeled proteins in the gel were detected by a simple chemiluminescence assay. The gel holder was placed on top of a sheet of x-ray film under safe lights. A solution of urea peroxide (3.6%) in 0.4M $HNO_3$ was layered over the gel in the holder and allowed to stand for 20 min. The solution was aspirated out of the holder and 15 mL of 0.25M NaOH was added to initiate light emission. exposed to X-ray film for 15 min. FIGS. 3A and 3B demonstrate the detection of the labeled proteins BSA—APNa2 and BSA—$APCN_2$, respectively directly in the gel. Light emission grew in over a period of several seconds, rose to a maximum and decayed over several minutes.

30. Sensitivity of Detecting of Labeled Proteins.

Solutions of the labeled proteins BSA—$APNa_2$ and BSA—$APCN_2$ containing between $10^{-11}$ and $10^{-17}$ moles of labeled protein were prepared in 0.1M tris buffer, pH 8.8. Ten $\mu$L aliquots were each added to 50 $\mu$L of 3.6% urea peroxide in 0.4 M HCl and incubated for 2 min at 25° C. Chemiluminescence was initiated by adding 100 $\mu$L of 0.25M NaOH to each of these solutions. Total light intensity values were measured by single determinations. Background light levels were 0.017 for both BSA—$APCN_2$ and BSA—$APNa_2$ under these conditions.

TABLE 7

| BSA-$APCN_2$ | | BSA-$APNa_2$ | |
| --- | --- | --- | --- |
| Moles Protein | I Total | Moles Protein | I Total |
| $6.5 \times 10^{-11}$ | 9720 | $2.4 \times 10^{-11}$ | 9230 |
| $6.5 \times 10^{-12}$ | 1930 | $4.8 \times 10^{-12}$ | 1730 |
| $6.5 \times 10^{-13}$ | 93.1 | $4.8 \times 10^{-13}$ | 101 |
| $6.5 \times 10^{-14}$ | 9.68 | $4.8 \times 10^{-14}$ | 7.62 |
| $6.5 \times 10^{-15}$ | 1.86 | $4.8 \times 10^{-15}$ | 0.81 |
| $6.5 \times 10^{-16}$ | 1.55 | $4.8 \times 10^{-16}$ | 0.18 |
| $6.5 \times 10^{-17}$ | 0.14 | $4.8 \times 10^{-17}$ | 0.11 |

The foregoing description and examples are illustrative only and not to be considered as restrictive. It is recognized that modifications of the specific compounds and methods not specifically disclosed can be made without departing from the spirit and scope of the present invention. The scope of the invention is limited only by the appended claims.

What is claimed is:

1. A chemiluminescent compound of the formula:

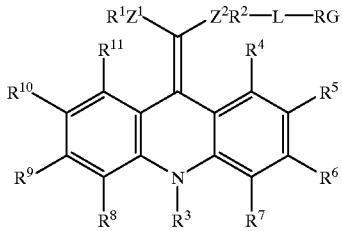

wherein $Z^1$ and $Z^2$ are independently selected from O, S and $NR^{12}$, $R^{12}$ is selected from alkyl, aryl, alkylsulfonyl and arylsulfonyl groups, $R^1$ is a group containing from 1 to about 50 non-hydrogen atoms which is removable by an acid and $R^2$ and $R^3$ are organic groups containing from 1 to 50 non-hydrogen atoms selected from C, N, O, S, P and halogen atoms, $R^4$–$R^{11}$ are independently selected from hydrogen and substituents which do not interfere with the generation of chemiluminescence, L is a linking group selected from a bond, divalent groups and polyvalent groups, and RG is a reactive group selected from carboxyl, carboxyl ester, acid anhydride, acid chloride, acyl azide, aldehyde, chloroformate, amine, hydroxyl, hydrazine, isocyanate, isothiocyanate, sulfonyl chloride, $SO_2CH_2CF_3$, tosyl, maleimide, N-hydroxy-succinimide ester, aziridine, imine, disulfide

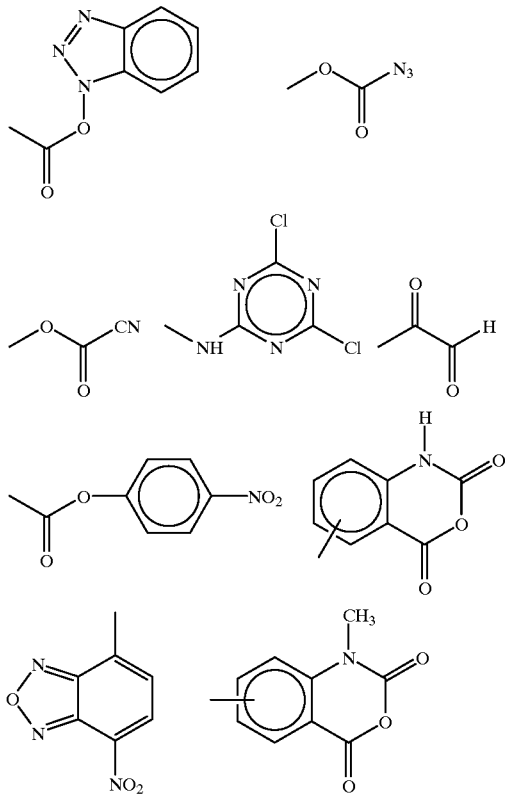

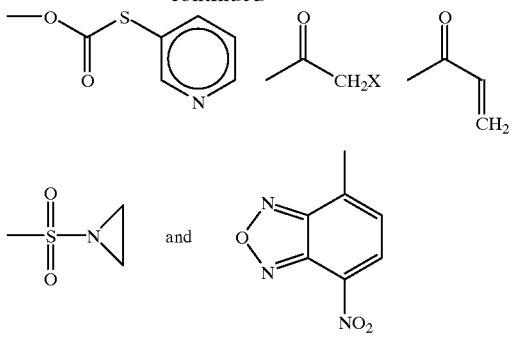

wherein X is selected from chlorine bromine and iodine.

2. The compound of claim 1 wherein the groups $Z^1$ and $R^1$ are combined to form a phosphate group OPO(OR')(OR''), R' and R'' are independently selected from alkyl groups, substituted alkyl groups and alkali metal ions and the compound has the formula

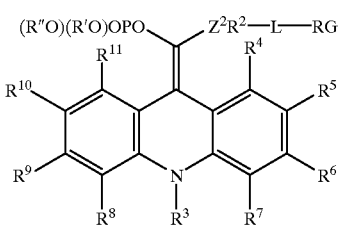

3. The compound of claim 2 wherein R' and R'' are each a 2-cyanoethyl group.

4. The compound of claim 2 wherein R' and R'' are each alkali metal ions.

5. The compound of claim 1 wherein $Z^2$ is O or S, and $R^2$ is selected from phenyl and substituted phenyl groups.

6. The compound of claim 5 wherein each of the groups $R^4$–$R^{11}$ is a hydrogen, $R^3$ is methyl, $Z^1$ and $R^1$ are combined to form a phosphate group —$OPO_3M_2$, and each M is an alkali metal ion and the compound has the formula

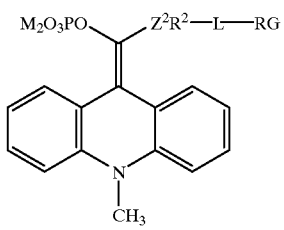

7. The compound of claim 1 wherein the groups $Z^2$ and $R^2$—L—RG are combined to form a phosphate group OPO(OR') (O—L—RG), R' is independently selected from alkyl groups, substituted alkyl groups, hydrogen and alkali metal ions and the compound has the formula:

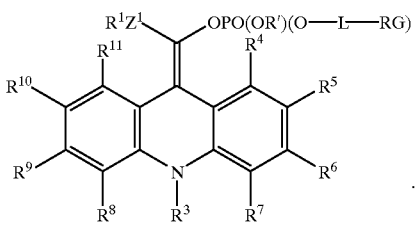

8. The compound of claim 7 wherein $Z^1$ is S and $R^1$ is phenyl.

9. The compound of claim 1 wherein L is a divalent group containing from 1 to 30 non-hydrogen atoms selected from C, N, O, P and S atoms.

10. The compound of claim 1 wherein the reactive group RG is selected from OH, $NH_2$, COOH, $SO_2CH_2CF_3$, N-hydroxysuccinimide ester and maleimide groups.

11. A chemiluminescent labeled compound comprising a conjugate of a compound to be detected and a compound of the formula

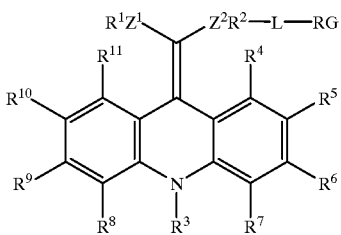

wherein $Z^1$ and $Z^2$ are independently selected from O, S and $NR^{12}$, $R^{12}$ is selected from alkyl, aryl, alkylsulfonyl and arylsulfonyl groups, $R^1$ is a group containing from 1 to about 50 non-hydrogen atoms which is removable by an acid and $R^2$ and $R^3$ are organic groups containing from 1 to 50 non-hydrogen atoms selected from C, N, O, S, P and halogen atoms, $R^4$–$R^{11}$ are independently selected from hydrogen and substituents which do not interfere with the generation of chemiluminescence, L is a linking group selected from a bond, divalent groups and polyvalent groups, and RG is a reactive group and the compound to be detected is an analyte or a specific binding pair member.

12. The chemiluminescent labeled compound of claim 11 wherein the groups $Z^1$ and $R^1$ are combined to form a phosphate group OPO(OR')(OR''), and R' and R'' are independently selected from alkyl groups, substituted alkyl groups and alkali metal ions.

13. The chemiluminescent labeled compound of claim 12 wherein R' and R'' are each a 2-cyanoethyl group.

14. The chemiluminescent labeled compound of claim 12 wherein R' and R'' are each alkali metal ions.

15. The chemiluminescent labeled compound of claim 11 wherein $Z^2$ is O or S, and $R^2$ is selected from phenyl and substituted phenyl groups.

16. The chemiluminescent labeled compound of claim 15 wherein each of the groups $R^4$–$R^{11}$ is a hydrogen, $R^3$ is methyl, $Z^1$ and $R^1$ are combined to form a phosphate group—$OPO_3M_2$, and each M is an alkali metal ion.

17. The chemiluminescent labeled compound of claim 11 wherein the groups $Z^2$ and $R^2$—L—RG are combined to form a phosphate group OPO (OR') (O—L—RG), and R' is independently selected from alkyl groups, substituted alkyl groups, hydrogen and alkali metal ions.

18. The chemiluminescent labeled compound of claim 17 wherein $Z^1$ is S and $R^1$ is phenyl.

19. The chemiluminescent labeled compound of claim 11 wherein L is a divalent group containing from 1 to 30 non-hydrogen atoms selected from C, N, O, P and S atoms.

20. The chemiluminescent labeled compound of claim 11 wherein the reactive group is selected from OH, $NH_2$, COOH, $SO_2CH_2CF_3$, N-hydroxy-succinimide ester and maleimide groups.

21. The chemiluminescent labeled compound of claim 11 wherein the the compound to be detected is the analyte and is selected from drugs, hormones, pesticides, pesticide metabolites, DNA, RNA, oligonucleotides, antibodies, and antigens.

22. The chemiluminescent labeled compound of claim 11 wherein the compound to be detected is the specific binding partner and is selected from antigens, antibodies, haptens, oligo-nucleotides, polynucleotides, avidin, streptavidin, hormones, receptors, lectins, carbohydrates, IgG, protein A, and nucleic acid binding proteins.

* * * * *